US010064684B2

(12) United States Patent
Nakamura et al.

(10) Patent No.: US 10,064,684 B2
(45) Date of Patent: Sep. 4, 2018

(54) OPERATION-MODE INDICATING SYSTEM FOR BODY SUPPORT APPARATUS, AND BODY SUPPORT APPARATUS

(71) Applicants: DENSO CORPORATION, Kariya, Aichi-pref. (JP); SHINSHU UNIVERSITY, Matsumoto, Nagano-pref. (JP); TOKYO WOMEN'S MEDICAL UNIVERSITY, Tokyo (JP)

(72) Inventors: Satoru Nakamura, Kariya (JP); Minoru Takahashi, Tokoname (JP); Kazuhiro Hongo, Matsumoto (JP); Tetsuya Goto, Matsumoto (JP); Yosuke Hara, Matsumoto (JP); Jun Okamoto, Tokyo (JP)

(73) Assignees: DENSO CORPORATION, Kariya (JP); SHINSHU UNIVERSITY, Matsumoto (JP); TOKYO WOMEN'S MEDICAL UNIVERSITY, Tokyo (JP)

( * ) Notice: Subject to any disclaimer, the term of this patent is extended or adjusted under 35 U.S.C. 154(b) by 1183 days.

(21) Appl. No.: 14/249,488

(22) Filed: Apr. 10, 2014

(65) Prior Publication Data
US 2014/0343369 A1 Nov. 20, 2014

(30) Foreign Application Priority Data

Apr. 11, 2013 (JP) ................................. 2013-083074

(51) Int. Cl.
*A61B 90/60* (2016.01)
*F16M 11/04* (2006.01)
(Continued)

(52) U.S. Cl.
CPC .............. *A61B 19/28* (2013.01); *A61B 90/30* (2016.02); *A61B 90/60* (2016.02); *F16M 11/04* (2013.01); *A61B 90/20* (2016.02)

(58) Field of Classification Search
CPC ................................. A61B 90/60; F16M 11/04
(Continued)

(56) References Cited

U.S. PATENT DOCUMENTS 4,912,388 A 3/1990 Tanaka et al.
6,494,827 B1 12/2002 Matsumoto et al.
(Continued)

FOREIGN PATENT DOCUMENTS

JP 55-134816 A 10/1980
JP H02-231394 A 9/1990
(Continued)

*Primary Examiner* — David Bates
(74) *Attorney, Agent, or Firm* — Posz Law Group, PLC

(57) ABSTRACT

In an operation-mode indicating system, a first light emitting device is located within a peripheral visual field of an operator and is controllably connected to a controller. The peripheral visual field is defined around a center visual field of the operator while the operator is looking at a predetermined site. A body support apparatus is capable of performing an operation to the predetermined site. The controller controls the first light emitting device to emit first light in a first operation mode of the body support apparatus and second light in a second operation mode of the body support apparatus. The first light and the second light are visually distinguishable from each other.

14 Claims, 13 Drawing Sheets

(51) Int. Cl.
    *A61B 19/00*     (2006.01)
    *A61B 90/30*     (2016.01)
    *A61B 90/20*     (2016.01)

(58) Field of Classification Search
    USPC .......................................... 248/118; 700/60
    See application file for complete search history.

(56) References Cited

U.S. PATENT DOCUMENTS

| | | | |
|---|---|---|---|
| 9,486,289 B2* | 11/2016 | Okuda | ................... A61B 90/60 |
| 2009/0036901 A1 | 2/2009 | Omori | |
| 2010/0268221 A1 | 10/2010 | Beller et al. | |
| 2011/0295165 A1 | 12/2011 | Cavallaro et al. | |
| 2014/0014804 A1 | 1/2014 | Okuda et al. | |

FOREIGN PATENT DOCUMENTS

| | | |
|---|---|---|
| JP | H07-125980 A | 5/1995 |
| JP | H08-245166 A | 9/1996 |
| JP | H09-173279 A | 7/1997 |
| JP | 2001-083434 A | 3/2001 |
| JP | 2005-087617 A | 4/2005 |
| JP | 2009-291363 A | 12/2009 |
| JP | 2014-018321 A | 2/2014 |

\* cited by examiner

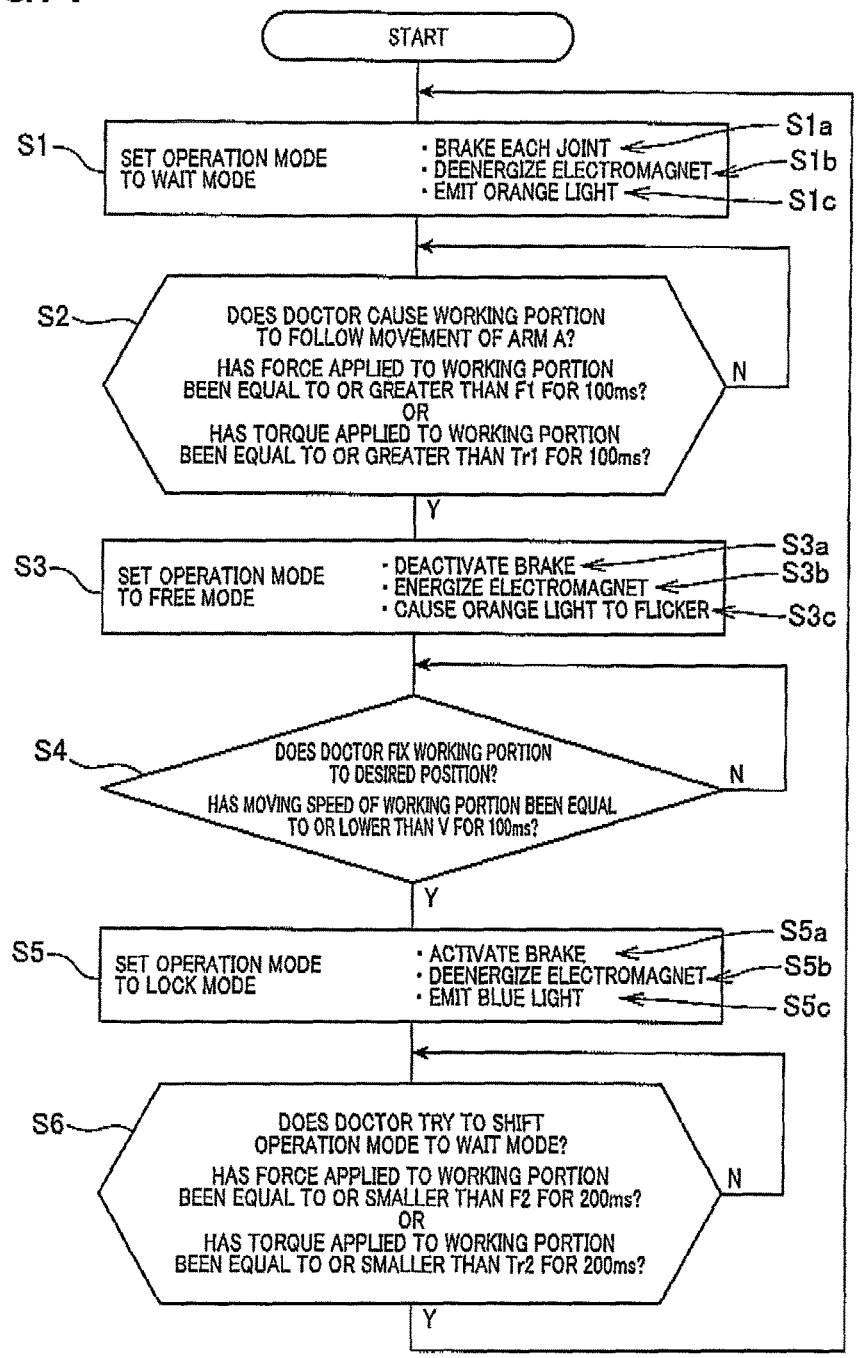

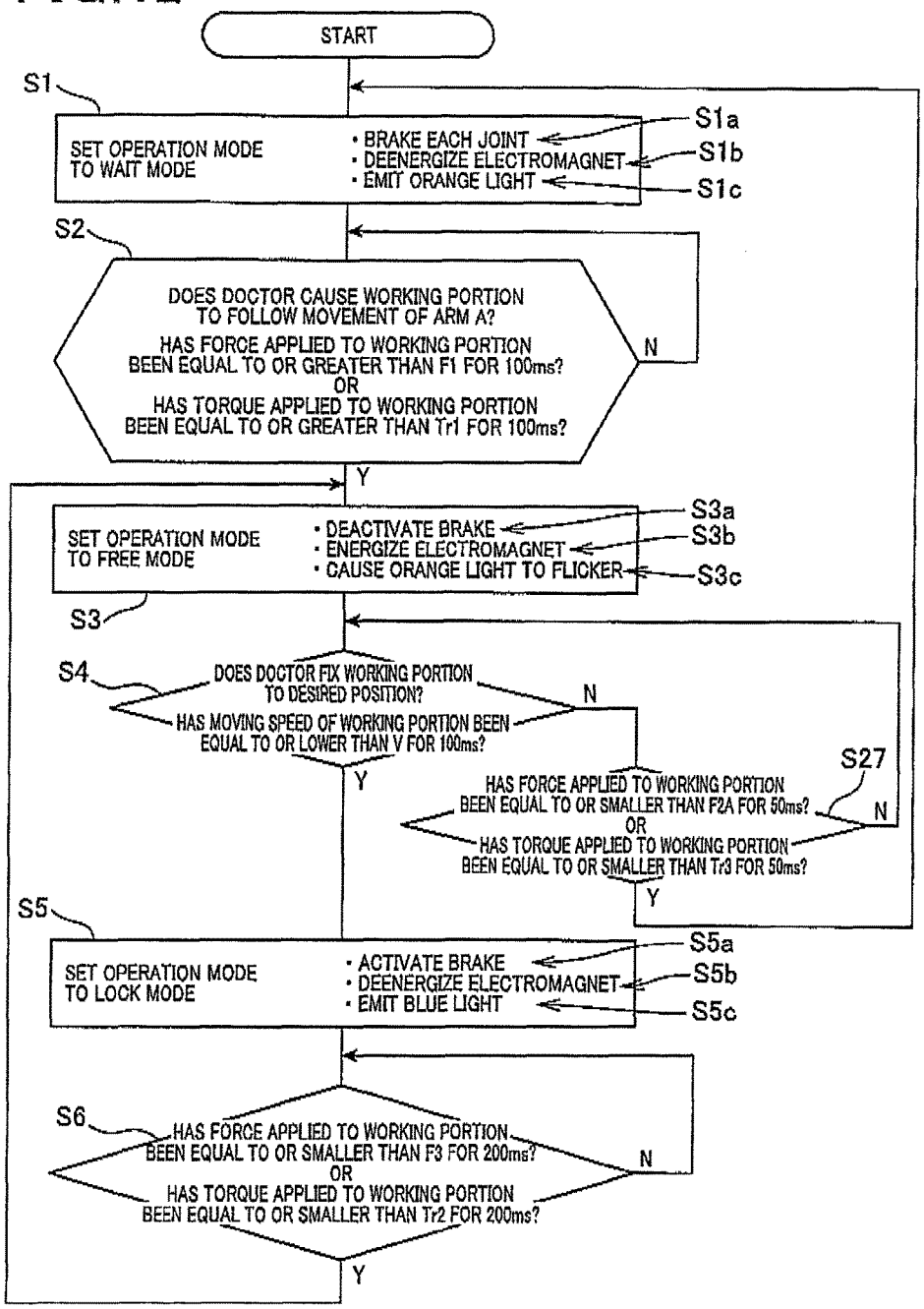

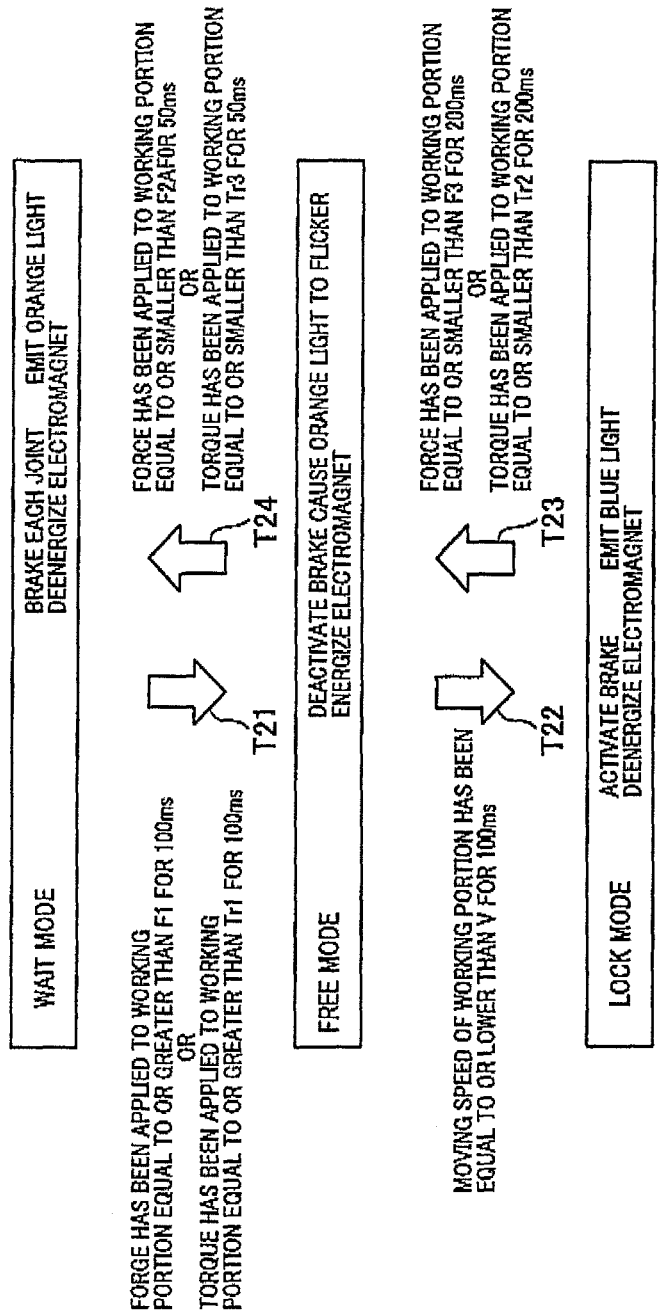

OPERATION-MODE INDICATING SYSTEM FOR BODY SUPPORT APPARATUS, AND BODY SUPPORT APPARATUS

CROSS REFERENCE TO RELATED APPLICATIONS

This application is based on and claims the benefit of priority from Japanese Patent Application 2013-083074 filed on Apr. 11, 2013, the disclosure of which is incorporated in its entirety herein by reference.

TECHNICAL FIELD

The present disclosure relates to body support apparatuses that support a part of an operator's body and follow motion of the supported part of the operator's body. In addition, the present disclosure relates to operation-mode indicating system for indicating an operation mode of a body support apparatus.

BACKGROUND

For precise and/or long manual operations, such as surgical operations and the like, there are known body support apparatuses for supporting a part of an operator's body, such as an arm. Such a body support apparatus is required to make an arm support supporting an operator's arm follow motion of the supported arm, and lock the arm support when the operator wants to fix the supported arm.

In order to meet such requirements, there are known body support apparatuses, an example of which is disclosed in Japanese Patent Application Publication No. 2009-291363, referred to as a first patent application.

The body support apparatus disclosed in the first patent application is configured to switch its operation mode between a lock mode and a free mode according to an operator's operation of a foot switch and/or the level of force; the level of force is applied from the supported arm to the arm support, and is measured by a sensor. In the lock mode, the arm support is locked so that the operator does not move the supported arm. In the free mode, the arm support is freely movable so that the operator freely moves the supported arm.

For example, when the operator moves the supported arm to a desired position, and thereafter weakens force applied from the supported arm to the arm support, the sensor measures the change of the force applied to the arm support. In response to the measured result indicative of the change of the force applied to the arm support, a controller activates a brake to thereby lock the arm support to the desired position.

On the other hand, there is known a technology that indicates whether an operation lever for stopping motion of a bendable portion of an endoscope is locked or not, an example of which is disclosed in Japanese Patent Application Publication No. H09-173279, referred to as a second patent application.

In the second patent application, an indicator, which indicates whether the operation lever is locked or not, is provided in the operation lever.

SUMMARY

However, in the technology disclosed in the second patent application, an operator has to look at the operation lever in order to check whether the operation lever is locked or not.

For this reason, even if the apparatus disclosed in the second patent application were applied to the body support apparatus disclosed in the first patent application, an operator, who performs precise operations at a field by an arm supported by the arm support, could have to look aside from the field in order to check whether the operation lever is locked or not. This could result in interruption of the precise operations each time the operator turns the operator's eyes to the operation lever, reducing the operator's operation efficiency. If the operator performed precise operations without knowing whether the operation lever was locked or not, the operator might feel less focused on the precise operations.

Precise surgical operations, such as micrographic surgeries, are often performed in a very confined space, so that an assistant may touch the body support apparatus. Therefore, there is a need for a technology that permits the assistant to easily know the operation mode of the body support apparatus.

In view of the circumstances set forth above, one aspect of the present disclosure seeks to provide operation-mode indicating systems for a body support apparatus; each of the operation-mode indicating systems is capable of achieving the issues set forth above.

Specifically, an alternative aspect of the present disclosure aims to provide such operation-mode indicating systems, each of which permits an operator to easily check the operation mode of the body support apparatus without taking the operator's eyes off a field to be operated.

Additionally, the alternative aspect of the present disclosure aims to provide these operation-mode indicating systems, each of which permits an assistant to easily check the operation mode of the body support apparatus.

A further aspect of the present disclosure aims to provide body support apparatuses, each of which is provided with one of the operation-mode indicators according to the aspects of the present disclosure.

According to a first exemplary aspect of the present disclosure, there is provided an operation-mode indicating system for a body support apparatus for performing an operation to a predetermined site of an object. The body support apparatus includes a mount portion on which a part of a body of an operator is mountable, a support member that has at least one joint and supports the mount portion to be movable by bend of the at least one joint, and a fixing member controllable to, when the part of the body is mounted on the mount portion, fix the mount portion to the part of the body to thereby cause the mount portion to follow movement of the part of the body. The body support apparatus includes a limiting member controllable to limit the bend of the at least one joint to limit movement of the mount portion. The operation-mode indicating system includes a controller controllably connected to the fixing member and the limiting member and switchably setting an operation mode of the body support apparatus in one of a first operation mode and a second operation mode. In the first operation mode, the controller controls the fixing member to fix the mount portion to the part of the body, and controls the liming member not to limit the bend of the at least one joint to thereby cause the mount portion to be freely movable. In the second control mode, the controller controls the fixing member to release a fixture of the mount portion to the part of the body, and controls the limiting member to limit the bend of the at least one joint to thereby limit movement of the mount portion. The operation-mode indicating system includes a first light emitting device located within a peripheral visual field of the operator and controllably connected to the controller. The peripheral visual field is defined around a center visual field of the operator while the operator is looking at the predetermined site. The controller controls the first light emitting device to emit first light in the first operation mode and second light in the second operation mode. The second light is visually distinguishable from the first light.

In the second exemplary aspect of the present disclosure, there is provided a body support apparatus for performing an operation to a predetermined site of an object. The body support apparatus includes a mount portion on which a part of a body of an operator is mountable, a support member that has at least one joint and supports the mount portion to be movable by bend of the at least one joint, and a fixing member controllable to, when the part of the body is mounted on the mount portion, fix the mount portion to the part of the body to thereby cause the mount portion to follow movement of the part of the body. The body support apparatus includes a limiting member controllable to limit the bend of the at least one joint to limit movement of the mount portion. The body support apparatus includes a controller controllably connected to the fixing member and the limiting member and switchably setting an operation mode of the body support apparatus in one of a first operation mode and a second operation mode. In the first operation mode, the controller controls the fixing member to fix the mount portion to the part of the body, and controls the liming member not to limit the bend of the at least one joint to thereby cause the mount portion to be freely movable. In the second control mode, the controller controls the fixing member to release a fixture of the mount portion to the part of the body, and controls the limiting member to limit the bend of the at least one joint to thereby limit movement of the mount portion. The operation-mode indicating system includes a first light emitting device located within a peripheral visual field of the operator and controllably connected to the controller. The peripheral visual field is defined around a center visual field of the operator while the operator is looking at the predetermined site. The controller controls the first light emitting device to emit first light in the first operation mode and second light in the second operation mode. The second light is visually distinguishable from the first light.

In each of the first and second exemplary aspects of the present disclosure, the first light emitting device, which is located within the peripheral visual field of the operator who is looking at the predetermined site, emits the first light for the first operation mode, and emits the second light for the second operation mode that is visually distinguishable from the first light. This configuration permits the operator to recognize the first light by the peripheral visual field without taking the operator's gaze from the predetermined site to which the operator performs an operation. This makes it possible for the operator to successfully concentrate the operation to the predetermined site.

Various aspects of the present disclosure can include and/or exclude different features, and/or advantages where applicable. In addition, various aspects of the present disclosure can combine one or more feature of other embodiments where applicable. The descriptions of features, and/or advantages of particular embodiments should not be construed as limiting other embodiments or the claims.

BRIEF DESCRIPTION OF THE DRAWINGS

Other aspects of the present disclosure will become apparent from the following description of embodiments with reference to the accompanying drawings in which:

FIG. 4 is a flowchart schematically illustrating a mode determination task carried out by a controller illustrated in FIG. 1;

FIG. 12 is a flowchart schematically illustrating a mode determination task carried out by a controller according to the fifth embodiment of the present disclosure; and FIG. 13 is a mode transition view schematically illustrating how an operation mode of the body support apparatus changes according to the fifth embodiment.

DETAILED DESCRIPTION OF EMBODIMENT

Figure 1:
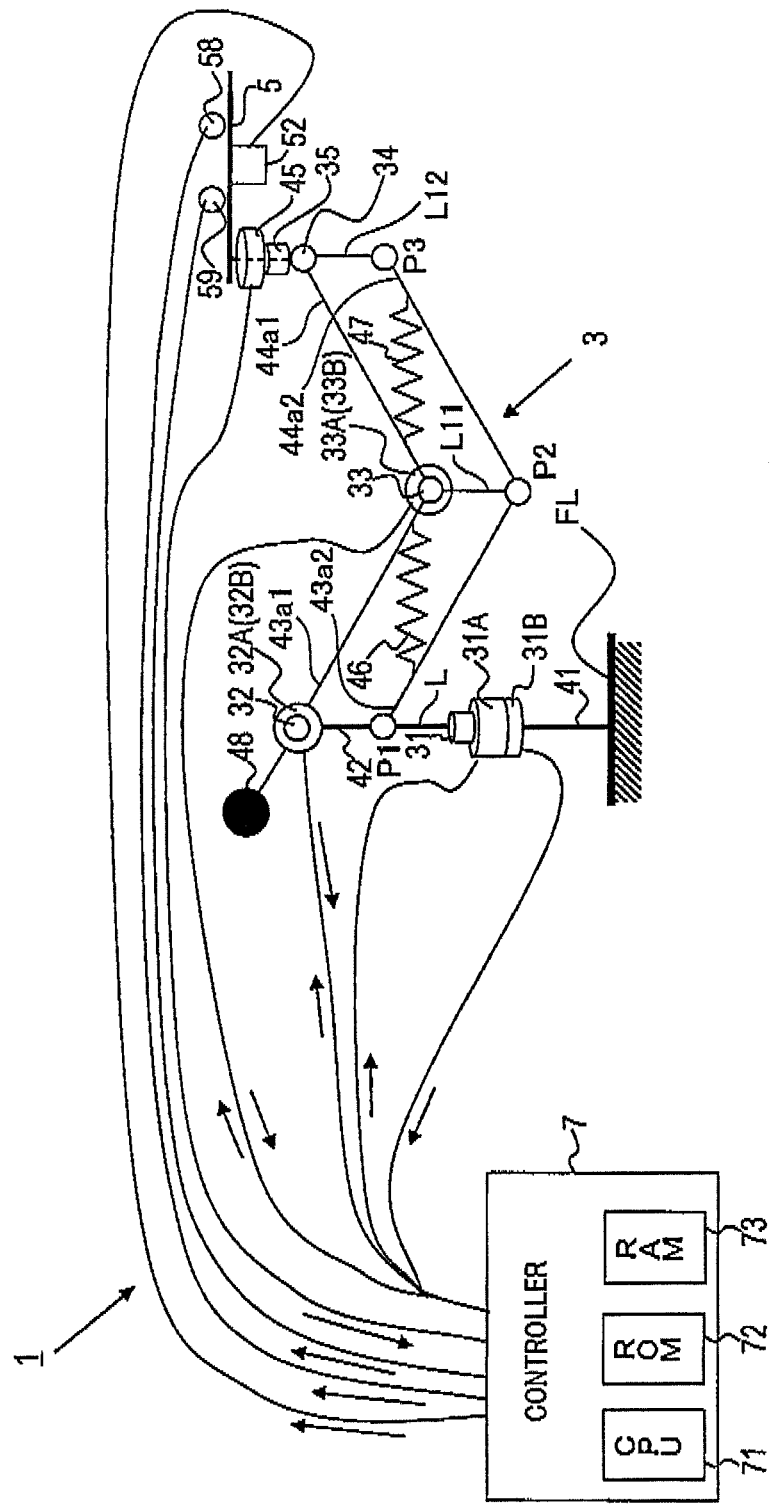
FIG. 1 is a schematic view of a body support apparatus and an operation-mode indicating system according to the first embodiment of the present disclosure.

Embodiments of the present disclosure will be described hereinafter with reference to the accompanying drawings. In the drawings, identical reference characters are utilized to identify identical corresponding components. In each of the following embodiments, there is described a body support apparatus for supporting an arm A of a doctor as an example of operators, who performs medical operations, such as surgical operations. However, body support apparatuses according to the present disclosure can be designed to support a part of the body of an operator who performs precise and/or long operations during a process of, for example, manufacturing a machine, such as precision machines. As a part of the body of an operator in addition to an arm, a hand, one or more fingers, a leg, a chin, or the like can be supported by the body support apparatuses.

First Embodiment

Figure 2A:
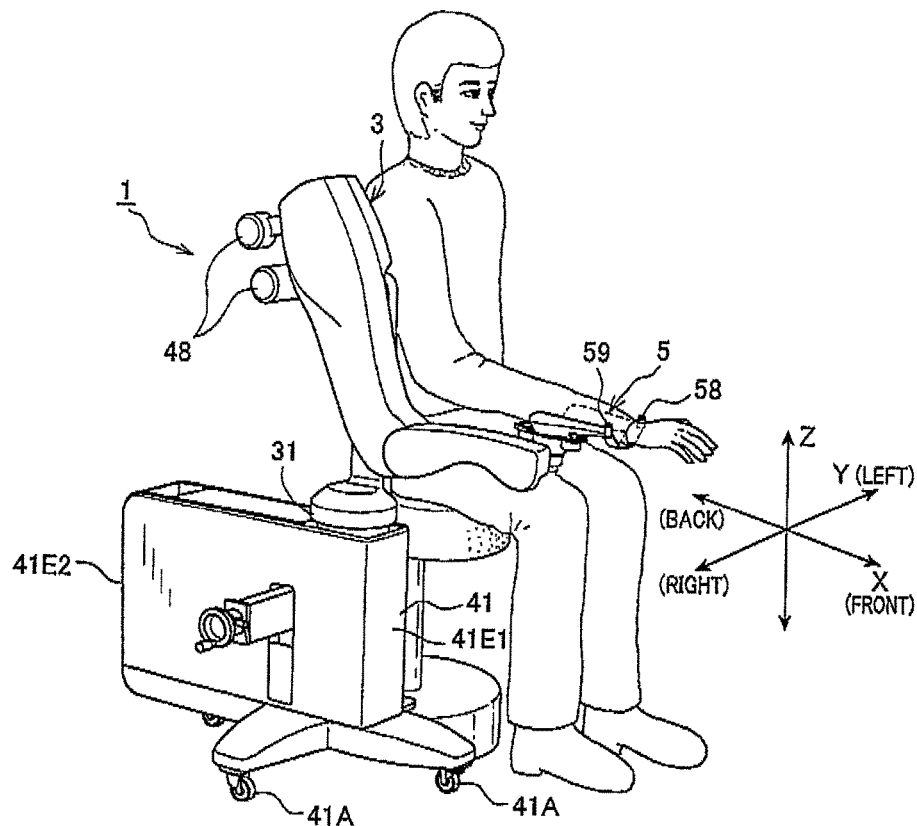
FIG. 2A is a perspective view schematically illustrating the outward appearance of the body support apparatus according to the first embodiment.

FIG. 1 illustrates a schematic view of a body support apparatus 1 and an operation-mode indicating system that is integrally installed in the body support apparatus 1 according to the first embodiment of the present disclosure, and FIG. 2A illustrates the outward appearance of the body support apparatus 1.

Referring to FIGS. 1 and 2A, the body support apparatus 1 is equipped with a multijoint arm 3, a working portion 5 for holding an arm A of a doctor attached to the multijoint arm 3, and a supporting base 41 for supporting the multijoint arm 3. The body support apparatus 1 is also equipped with a chair 6 for doctors, and a controller 7 serving as a controller for controlling motion of each of the multijoint arm 3 and the working portion 5.

The multijoint arm 3 is designed as a movement mechanism that movably supports the working portion 5 according to external force applied to the working portion 5. Specifically, the multijoint arm 3 has, for example, five rotational joints 31, 32, 33, 34, and 35 that provide five degrees of freedom.

The supporting base 41, having a substantially rectangular box shape, is located on a floor FL of an operating room, and configured to support the multijoint arm 3. For example, the supporting base 41 is equipped with casters 41A located at a bottom portion thereof, so that the supporting base 41 is easily movable on the floor FL. The supporting base 41 also has a stopper (not shown) provided for each of the casters 41A. A doctor or an assistant manipulates the stopper for each caster 41A to stop the movement of the caster 41A. This makes it possible to fixedly locate the supporting base 41 at a desired position of the floor FL.

The joint 31 has a vertical axis orthogonal to, for example, the floor FL, and is mounted on a first longitudinal end of a top surface of the supporting base 41 such that the vertical axis is orthogonal to the top surface. The first longitudinal end of the supporting base 41 will be referred to as a front end 41E1 thereof. A second longitudinal end of the supporting base 41, which is opposite to the first longitudinal end, will be referred to as a back end 41E2 thereof. Thus, a direction in front of the first longitudinal end 41E1 will be referred to as a front direction of the supporting base 41, and a direction opposite to the front direction will be referred to as a back direction of the supporting base 41. On the basis of the front and bask directions of the supporting base 41, the right and left directions of the supporting base 41 are also defined (see FIG. 2A).

For example, as illustrated in FIG. 2A, the chair 6 is located on the floor FL on the left side of the supporting base 41. On the chair 6, a doctor can be seated while looking toward the front direction of the supporting base 41 in order to perform surgical operations. Thus, the front and back directions and the right and left directions of the supporting base 41 correspond to the front and back directions and the right and left directions of a doctor who is seated on the chair 6.

In FIG. 2A, the front-back direction, the left-right direction, and the vertical direction of the supporting base 41 illustrated by respective arrows X, Y, and Z.

On the joint 31, a first end of a link L is so mounted. On the second end of the link L opposite to the first end, a shoulder portion 42 is mounted to extend upwardly from the second end of the link L such that the joint 32 is located at a top end of the shoulder portion 42. The shoulder portion 42 and the link L are rotatable about the vertical axis of the joint 31. To the joint 31, a brake, such as an electromagnetic brake, 31A is attached for reducing rotation of the shoulder portion 42 relative to the supporting base 41 around the vertical axis of the joint 31. To the joint 31, an encoder 31B is attached for measuring an amount of rotation of the shoulder portion 42 relative to the supporting base 41.

The multijoint arm 3 also includes a first arm member 43 having a first end and a second end opposite thereto. The joint 32 has a horizontal axis orthogonal to the vertical axis of the joint 31; the horizontal axis is parallel to an X-Y plane defined by the X (front-back) directions and the Y (left-right) directions). The first end of the first arm member 43 is attached to the joint 32 and the shoulder portion 42 such that the first arm member 43 is swingable about the horizontal axis of the joint 32. The joint 33 having a horizontal axis parallel to the horizontal axis of the joint 32 is attached to the second end of the first arm member 43.

For example, the first arm member 43 is designed as a parallel link mechanism comprised of a set of first and second links 43a1 and 43a2. The first and second links 43a1 and 43a2 are configured to move while keeping the first and second links 43a1 and 43a2 in parallel to each other with a constant space therebetween. One end of the first link 43a1 is joined to the joint 32 to be swingable about the horizontal axis of the joint 32. One end of the second link 43a2 is also joined to a pivot point P1 to be swingable about a horizontal axis of the pivot point P1 parallel to the horizontal axis of the joint 32; the pivot point P1 is attached to the second end of the link L. The other end of the first link 43a1 is joined to the joint 33 to be swingable about the horizontal axis of the joint 33. The other end of the second link 43a2 is also joined to a pivot point P2 to be swingable about a horizontal axis of the pivot point P2; the horizontal axis of the pivot point P2 is parallel to the horizontal axis of the joint 33.

The multijoint arm 3 further includes a second arm member 44 having a first end and a second end opposite thereto. The first end of the second arm member 44 is attached to the joint 33 such that the second arm member 44 is swingable about the horizontal axis of the joint 33. The joint 34 having a horizontal axis parallel to the horizontal axis of the joint 33 is attached to the second end of the second arm member 44.

For example, the second arm member 44 is designed as a parallel link mechanism comprised of a set of first and second links 44a1 and 44a2 configured to move while keeping the first and second links 44a1 and 44a2 in parallel to each other with a constant space therebetween. One end of the first link 44a1 is joined to the joint 33 to be swingable about the horizontal axis of the joint 33. One end of the second link 44a2 is also joined to the pivot point P2 to be swingable about the horizontal axis of the pivot point P2. The other end of the first link 44a1 is joined to the joint 34 to be swingable about the horizontal axis of the joint 34. The other end of the second link 44a2 is also joined to a pivot point P3 to be swingable about a horizontal axis of the pivot point P3; the horizontal axis of the pivot point P3 is parallel to the horizontal axis of the joint 34.

Note that the link L of the shoulder portion 42 connecting between the joint 32 and the pivot P1, and a link L11 connecting between the joint 33 and the pivot P2 are provided. The links L and L11 permit the parallel link mechanism of the first arm member 43 to move while maintaining a constant space therebetween. Similarly, there is a link L12 connecting between the joint 34 and the pivot P3. The links L11 and L12 permit the parallel link mechanism of the second arm member 44 to move while maintaining a constant space therebetween.

The working portion 5 has a first end and a second end in its length direction. To the joint 34, the first end of the working portion 5 is attached via the joint 35 such that a vertical axis of the joint 35 is orthogonal to the horizontal axis of the joint 34. Specifically, the working portion 5 is configured to be rotatable about the vertical axis of the joint 35. More specifically, the working portion 5 is joined to the joint 35 via a force sensor 45 to be rotatable about the vertical axis of the joint 35. The second end of the working portion 5 is designed as a free end.

The force sensor 45 is communicably connected to the controller 7, and operative to measure, as force data applied to the working portion 5, first force, second force, and third force respectively applied to the working portion 5 in a first axis, a second axis, and a third axis. The first, second, and third axes are defined at, for example, a predetermined point of the working portion 5 through which an extending line of the vertical axis of the joint 35 passes.

For example, the first axis is a length direction of the working portion 5 orthogonal to the vertical axis of the joint 35, the second axis is an axis orthogonal to the first axis and to the vertical axis of the joint 35, and the third axis corresponds to the vertical axis of the joint 35, which is orthogonal to the first axis and the second axis.

The force sensor 45 is also operative to measure, as torque data applied to the working portion 5, first torque about the first axis, second torque about the second axis, and third torque about the third axis.

The force sensor 45 is further operative to output the measured force data and measured torque data to the controller 7.

Like the joint 31, to the joint 32, a brake, such as an electromagnetic brake, 32A is attached for reducing rotation of the first arm member 43 relative to the shoulder portion 42 around the horizontal axis of the joint 32. To the joint 32, an encoder 32B is attached for measuring an amount of rotation of the first arm member 43 relative to the shoulder portion 42.

Additionally, to the joint 33, a brake, such as an electromagnetic brake, 33A is attached for reducing rotation of the second arm member 44 relative to the joint 33 around the horizontal axis of the joint 33. To the joint 33, an encoder 33B is attached for measuring an amount of rotation of the second arm member 44 relative to the joint 33.

Each of the brakes 31A to 33A is communicably connected to the controller 7, and can be controlled by the controller 7.

Each of the encoders 31B to 33B is communicably connected to the controller 7, and operative to output the measured amount of rotation to the controller 7.

Between the second link 43a2 of the first arm member 43 and the joint 33, a spring 46 is provided, and, between the second link 44a2 of the second arm member 44 and the joint 33, a spring 47 is provided. The one end of the first link 43a1 of the first arm member 43 extends through the joint 31 to be far from the joint 32 by a preset length. To the extending end of the first link 43a1 of the first arm member 43, counterweights 48 are attached.

The springs 46 and 47 and the counterweights 48 are operative to, when a doctor's arm A is mounted on the working portion 5, apply counterbalance force to the working portion 5 and the multijoint arm 3.

Specifically, biasing force from the springs 46 and 47 and the counterweights 48 biases the working portion 5 upward in parallel to the third axis. The biasing force applied to the working portion 5 counterbalances the sum of: the weight of the working portion 5 including electromagnets 52 described later; the weight of a doctor's arm A held by the working portion 5; the weight of a holder member 55 described later; and the weight of the multijoint arm 3. The sum of these weights will be referred to as an arm total weight hereinafter.

This balance supports the doctor's arm A mounted on the working portion 5. Note that the biasing force should be ideally counterbalanced to the arm total weight.

However, the doctor's arm A normally performs surgical operations to an affected site of a living body, such as a patient, from above. Thus, in consideration of this matter, the biasing force is determined to bias, with very weak force, the working portion 5 in the upward direction. Note that the upward direction means a direction relative to the affected site which is receiving surgical treatment from the doctor's arm A, and thereby treatment of the affected site can be safely performed while the working portion 5 is prevented from being unintentionally lowered. At least one of the springs 46 and 47 can be eliminated if the balance of force is established with the use of only the counterweights 48. One of various types of measures for biasing the working portion 5 can be used.

Figure 2B:
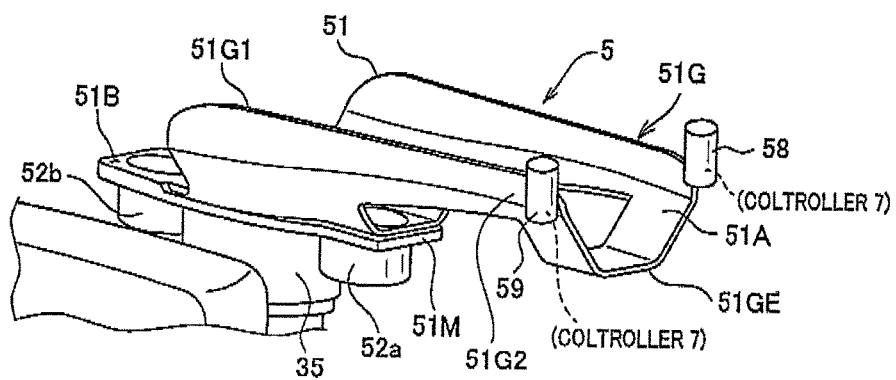
FIG. 2B is an enlarged perspective view of a working portion of the body support apparatus illustrated in FIG. 2A.
Figure 3A:
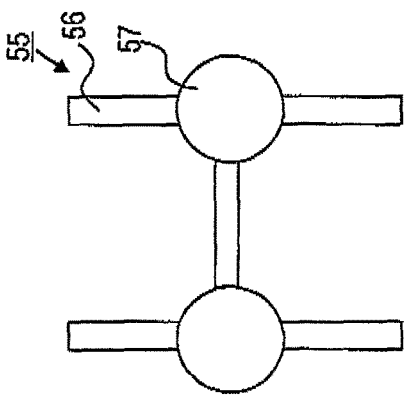
FIG. 3A is a plan view of a holder member that should be attached to an arm of a doctor according to the first embodiment.
Figure 3B:
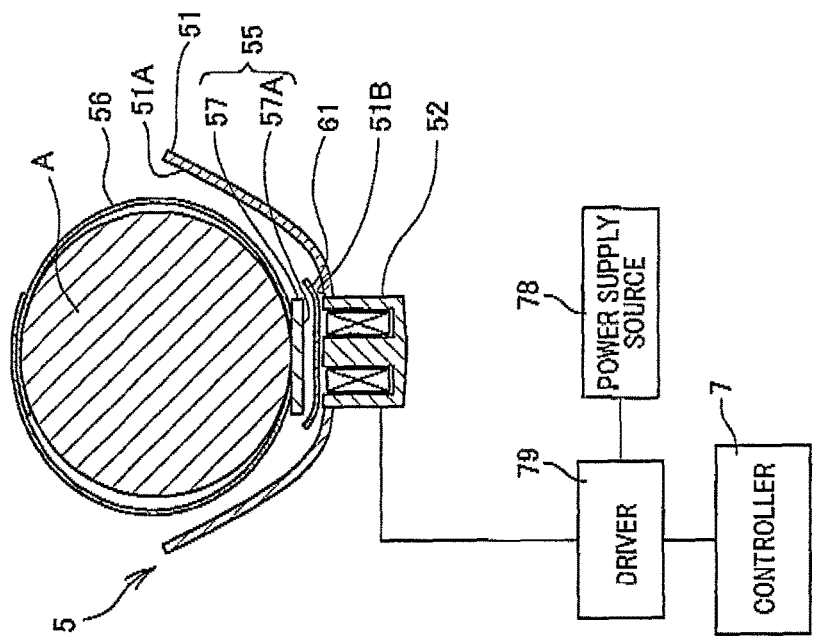
FIG. 3B is a cross sectional view schematically illustrating an example of the structure of the working portion.

Referring to FIGS. 2B, 3A, and 3B, while the holder member 55 is attached to an arm A of a doctor, the working portion 5 is configured to hold the doctor's arm A via the holder member 55.

As illustrated in FIGS. 3A and 3B, the holder member 55 is comprised of a first pair of flexible bands 56a1 and 56a2, a second pair of flexible bands 56b1 and 56b2, and a magnetic member 57 attached to the bands 56a1, 56a2, 56b1, and 56b2. The magnetic member 57 is comprised of: a pair of circular magnetic plates 57a and 57b each having a first circular surface and a second circular surface opposite thereto; and a bar member 57c having a predetermined length and joining the circular magnetic plates 57a and 57b.

The circular magnetic plate 57a is directly attached to one end of each of the bands 56a1 and 56a2 such that the bands 56a1 and 56a2 face each other across the corresponding circular magnetic plate 57a. Similarly, the circular magnetic plate 57b is directly attached to one end of each of the bands 56b1 and 56b2 such that the bands 56b1 and 56b2 face each other across the corresponding circular magnetic plate 57b.

The bands 56a1 and 56a2 of the first pair and the bands 56b1 and 56b2 of the second pair are wound around a doctor's arm A while the first circular surfaces of the circular magnetic plates 57a and 57b face the doctor's arm A, and the second circular surfaces thereof, to which reference numeral 57A is attached, are located outward to be flush with each other (see FIG. 33). A doctor should attach the holder member 55 to his/her arm A such that, when the doctor extends the arm A forward in the front direction thereof, the second circular surfaces 57A of the circular magnetic plates 57a and 57b are directed downward.

Referring to FIGS. 2B and 3B, the working portion 5 is comprised of an arm holder 51.

The arm holder 51 includes a rectangular plate-like mount base 51M having a top surface 513 serving as a mount surface on which a doctor's arm A attached with the holder member 55 is mountable. The mount base 51M is mounted at its middle portion on the joint 35 to be rotatable about the vertical axis of the joint 35.

The body support apparatus 1 is further equipped with a pair of electromagnets 52a and 52b each having, for example, cylindrical shape.

In a first longitudinal end of the mount base 51M, one axial end of the electromagnet 52a is embedded such that a top surface of the one axial end of the electromagnet 52a is exposed to be flush with the top surface 51B. Similarly, in a second longitudinal end of the mount base 51M, which is opposite to the first longitudinal end thereof, one axial end of the electromagnet 52b is embedded such that a top surface of the one axial end of the electromagnet 52b is exposed to be flush with the top surface 51B.

As illustrated in FIG. 2A, while the body support apparatus 1 is in an initial state, the multijoint arm 3 is located such that the first longitudinal end of the mount base 51M is directed to the front direction of the supporting base 41.

The arm holder 51 also includes an arm guide 51G. The arm guide 51G is comprised of a first guide part 51G1. The first guide part 51G1 is formed to extend outward and obliquely upward from both lateral sides of a part of the mount base 51M; this part of the mount base 51M includes the middle portion and the second longitudinal end.

The arm guide 51G is also composed of a second guide part 51G2. While the body support apparatus 1 is in the initial state, the second guide part 51G2 is configured to continuously extend from the first guide part 51G1 in the front direction of the supporting base 41 to be outwardly far from the first longitudinal end of the mount base 51M. An extending end 51GE of the second guide part 51G2 is formed with a mount portion on which a part of a hand of a doctor's arm A is mountable. That is, the extending end 51GE of the second guide 51G2 of the arm holder 51 serves as a working end of the working portion 5 for performing surgical operations using, for example, surgical operation tools. Thus, the extending end 51GE of the second guide 51G2 of the arm holder 51 will be referred to as a working end 51GE hereinafter.

In other words, the first guide part 51G1 is designed as a tapered sidewall located above the mount base 51M such that an inner surface 51A of the tapered sidewall is tapered from an upper edge of the tapered sidewall to the mount base 51M to thereby guide the second surfaces 57B of the circular magnetic plates 57a and 57b of the holder member 55 onto the mount surface 51B of the mount base 51M. The second guide part 51G2 is configured to support a portion of a doctor's arm A, which extends outwardly from the mount base 51M in the front direction of the mount base 51M.

A soft plastic sheet 61, which is omitted in illustration in FIG. 2B, is mounted on the mount surface 51B of the mount base 51B to reduce slide resistance between the mount surface 51B and the second surfaces 57A of the circular magnetic plates 57a and 57b of the holder member 55.

For example, the longitudinal length of the mount base 51M is determined such that the magnetic plates 57a and 57b of the holder member 55 can be mounted on the top ends of the electromagnets 52a and 52b of the working portion 5.

Specifically, a doctor, who is seated on the chair 6 on the left side of the supporting base 41, mounts the right arm, i.e. an arm A, to which the mount member 5 is attached, on the mount base 51M of the arm holder 51. During the mount process, the doctor determine the position of the arm member 5 such that the magnetic plates 57a and 57b of the holder member 55 are mounted respectively on the top ends of the electromagnets 52a and 52b of the working portion 5 in alignment with the top ends thereof.

A state where the magnetic plates 57a and 57b of the holder member 55 are mounted respectively on the top ends of the electromagnets 52a and 52b of the working portion 5 in alignment with the top ends thereof will be referred to as a ready state hereinafter.

In the ready state, when the electromagnets 52a and 52b are energized, magnetic attraction force between the magnetic plate 57a and the electromagnet 52a and that between the magnetic plate 57b and the electromagnet 52b fixedly support the doctor's arm A on the arm holder 51, that is, the working portion 5 of the multijoint arm 3. This permits the working portion 5 to follow movement of the doctor's arm A from left to right and up or down while changing the shape of the multijoint arm 3.

On the other hand, when the electromagnets 52a and 52b are deenergized, magnetic attraction force between the magnetic plate 57a and the electromagnet 52a and that between the magnetic plate 57b and the electromagnet 52b disappear, so that the doctor can freely move the arm A independently of the arm holder 51, i.e., the working portion 5. Particularly, the soft plastic sheet 61 reduces slide resistance of a sliding movement of the arm A in the longitudinal direction of the mount base 51M, i.e. in the front-back directions of the doctor. The soft plastic sheet 61 also reduces residual magnetic flux acting, from the electromagnets 52a and 52b, to the magnetic plates 57a and 57b of the holder member 55.

For controlling energization or deenergization of the electromagnets 52a and 52b of the working portion 5, the body support apparatus 1 is equipped with a power supply source 78 and drivers 79 in addition to the controller 7.

Referring to FIG. 3B, the drivers 79 are electrically connected to the respective electromagnets 52a and 52b, and also to the power supply source 78. As the drivers 79, for example, switching elements are used. Specifically, to the drivers 79, electrical power, such as a predetermined voltage, is applied. The controller 7 is configured to turn on the drivers 79 to apply the electrical power to the electromagnets 52a and 52b, thus energizing the electromagnets 52a and 52b. The controller 7 is also operative to turn off the drivers 79 to interrupt the supply of the electrical power to the electromagnets 52a and 52b, thus deenergizing the electromagnets 52a and 52b. For example, the controller 7, the power supply source 78, and the drivers 79 are installed in the supporting base 41 illustrated in FIG. 2A.

As illustrated in FIG. 2B, the body support apparatus 1 is further equipped with a first light source 58 for doctors and a second light source 59 mainly for assistants.

In the first embodiment, the first light source 58 is mounted on the upper left side of the working end 51GE of the second guide part 51G2 in the front direction of the supporting base 41 while it is viewed from a doctor, who is seated on the chair 6 located on the left side of the supporting base 41 and has his/her right arm A mounted on the arm holder 51 of the working portion 5.

Specifically, as illustrated in FIG. 2A, the body support apparatus 1 is, for example, configured to be used for a right-handed doctor who is seated on the chair 6 located on the left side of the supporting base 41 and is mounting the right arm A on the arm holder 51 of the working portion 5. Because a surgical operation tool, such as a scalpel, is held by the right hand of the right arm A mounted on the arm holder 51, the positional relationship between the doctor and the arm holder 51 defines where an affected site of a patient who should undergo surgical operations is located relative to the position of the working end 51GE of the second guide part 51G2, more specifically, relative to the position of the tip of the surgical operation tool, which is performing surgical operations to the affected site.

In other words, a region where an affected site of a patient who should undergo surgical operations can be located is previously determined based on the position of the working end 51GE of the second guide part 51G2, more specifically, based on the position of the tip of the surgical operation tool.

While the doctor is performing surgical operations using the surgical operation tool to the affected site, i.e. a surgical operation region, the doctor is looking at the affected site directly, or via a surgical microscope or an endoscope. Thus, a center visual field CVF of the doctor is located on the affected site, so that a peripheral visual field PVF of the doctor is defined around the center visual field of the doctor.

Figure 3C:
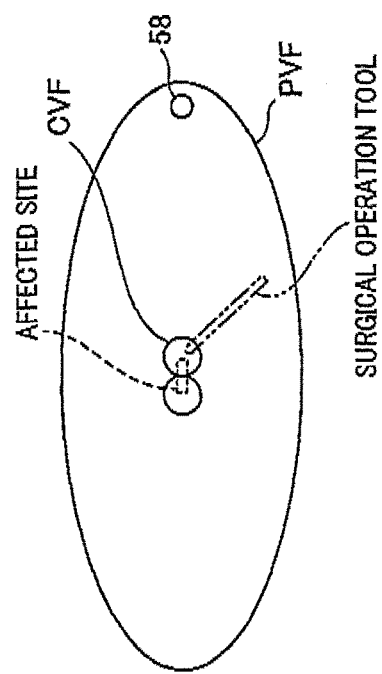
FIG. 3C is a view schematically illustrating a positional relationship between a peripheral visual field of the doctor and a first light source according to the first embodiment.

FIG. 3C schematically illustrates a peripheral visual field PVF of the doctor defined around the doctor's center visual field CVF via binocular eyepieces of a binocular surgical microscope while the doctor's right arm A is being supported by the arm holder 51 of the working portion 5. Note that, because the doctor is looking through the binocular eyepieces at an affected site, the two circular binocular eyepieces of the binocular surgical microscope are illustrated in FIG. 3C as the doctor's center visual field CVF.

For example, the doctor's horizontal view angle of the center visual field CVF is set to be within from 15 degrees to 30 degrees, and the doctor's vertical view angle of the center visual field CVF is set to be within from 8 degrees to 20 degrees. In the first embodiment, the peripheral visual field PVF is defined as a field around the center visual field CVF and, in the peripheral visual field PVF, the doctor, who is looking at the affected site by the center visual field CVF, can recognize colors contained in the peripheral visual field PVF. For example, as illustrated in FIG. 3C, the peripheral visual field PVF has a substantially ellipsoidal shape, and the ellipsoidal peripheral visual field PVF has a major axis and a minor axis that are determined depending on the doctor's horizontal and vertical view angles, respectively. For example, the doctor's horizontal view angle of the ellipsoidal peripheral visual field PVF is set to be within 120 to 180 degrees, and the doctor's vertical view angle of the ellipsoidal peripheral visual field PVF is set to be within 120 to 150 degrees.

Specifically, in the first embodiment, the first light source 58 has a special positional relationship with respect to the peripheral visual field PVF of the doctor with the right arm A being supported on the arm holder 51 such that the first light source 58 is located within the peripheral visual field PVF.

Specifically, in the first embodiment, the first light source 58 is mounted on the left-side of the working end 51GE of the second guide part 51G2 in the front direction of the supporting base 41 M (see FIG. 2B). This arrangement of the first light source 58 makes possible that the first light source 58 is located in a right-edge of the peripheral visual field PVF.

In addition, in the first embodiment, the second light source 59 is mounted on the right-side of the working end 51GE of the second guide part 51G2 in front direction of the supporting base 41 while it is viewed from the doctor who is seated on the chair 6. Preferably, as illustrated in FIGS. 23 and 3C, the second light source 59 is mounted on the right-side of the working end of the second guide part 51G2 in the front direction of the supporting base 41 M. This arrangement of the second light source 59 makes possible that the second light source 59 is located out of the peripheral visual field PVF.

This arrangement of the first light source 58 makes it possible for the doctor, who is performing surgical operations, to easily visually check the first light source 58. In addition, this arrangement of the second light source 59 makes it possible for an assistant, who is positioned on the right side of the supporting base 41, to easily visually check the second light source 59 while not interrupting the doctor.

The controller 7 is, for example, installed with an electronic control circuit equipped with a CPU 71, a ROM 72, and 1 RAM 73. When the body support apparatus 1 is powered on so that the controller 7 is activated, the CPU 71 receives the measured force data and the measured torque data sent from the force sensor 45, and the measured amount of rotation sent from each of the encoders 31B to 33B.

Then, the CPU 71 performs, based on the measured force and torque data and the measured amount of rotation, a mode determination task illustrated in FIG. 4 as a flowchart in accordance with at least one program stored in the ROM 72 and/or the RAM 73 using the memory space of the RAM 73.

Each of the first and second light sources 58 and 59 is electrically connected to the controller 7. Under control of the controller 7, each of the first and second light sources 58 and 59 is capable of normally emitting different colors of light, and causing a selected color of light to flash.

In the first embodiment, the controller 7, the first and second light sources 58 and 59, the power supply source 78, and the driver 79 serve as an operation-mode indicating system according to the first embodiment.

Next, operations of the mode determination task will be described hereinafter.

In order to perform surgical operations of an affected site of a patient mounted on a movable operating table (not shown), the movable operation table is located such that the affected site is located in the predetermined region determined based on the position of the working end 51GE of the second guide part 51G.

At that time, a doctor, who is going to perform the surgical operations, has the holder member 55 attached to the right arm A.

When starting the mode determination task, the CPU 71 sets the operation mode of the body support apparatus 1 to a wait mode in step S1. Specifically, the wait mode is designed assuming that no arms are mounted on the arm holder 51 of the working portion 5. That is, in the wait mode, the CPU 71 activates the brakes 31A, 32A, and 33A to stop movement of the corresponding joints 31, 32, and 33, respectively in step S1a. In addition, in step S1b, the CPU 71 turns off the drivers 79, thus deenergizing the electromagnets 52a and 52b. In step S1c, the CPU 71 instructs each of the first and second light sources 58 and 59 to emit continuous orange light.

Specifically, in the wait mode, the doctor can mount the right arm A on the arm holder 51 of the working portion 5, or can remove high/her right arm A mounted on the arm holder 51 therefrom. In addition, in the wait mode, because the joints 31 to 33 are stopped in movement by the corresponding brakes 31A to 33A, the position of the multijoint arm 3 is fixed even if the doctor removes the right arm A from the arm holder 51 of the working portion 5. At that time, because no brakes are provided in the joints 34 and 35, how the working end 51GE of the arm holder 51 of the working portion 5 is directed can be freely adjusted, so that where the affected site of the patient is located can be also adjusted depending on the position of the working end 51GE of the arm holder 51 of the working portion 5. The orange light emitted from the first light source 58 permits the doctor to easily know that the operating mode of the body support apparatus 1 is set in the wait mode.

Specifically, even if the doctor is performing surgical operations to the affected site of the patient using a surgical operation tool held by the right hand, it is possible for the doctor to easily know that the operating mode of the body support apparatus 1 is set in the wait mode. This is because the first light source 58 is located in the peripheral visual field PVF while the doctor is looking at the affected site so that the center visual field CVF is located on the affected site.

In addition, the orange light emitted from the second light source 59 permits one or more assistants to easily know that the operating mode of the body support apparatus 1 is set in the wait mode.

Next, the CPU 71 determines whether the doctor tries to move the right arm A to cause the working portion 5 to follow movement of the right arm A based on the measured force and torque data in step S2.

Specifically, when the doctor wants to positively make the working portion 5 follow movement of the right arm A, the doctor, who mounts the right arm A on the arm holder 51 of the working portion 5 in the ready state, performs a first action and thereafter a second action. The first action is to support the right arm A with the muscle of the right arm A, and the second action is to apply force to the arm holder 51 of the working portion 5 via the right arm A in for example a direction toward the floor FL.

In the first embodiment, a threshold level for force applied to the arm holder 51 of the working portion 5 during the first action will be referred to as an F2, and a threshold level for force applied to the arm holder 51 of the working portion 5 during the second action will be referred to as an F1.

Specifically, when the doctor wants to make the working portion 5 follow movement of the right arm A, the doctor performs the first action to support the right arm A with the muscle of the right arm A, thus applying weak force to the working portion 5 downward. Because the applied force is to merely support the right arm A, the applied force is normally equal to or smaller than the threshold level F2 of, for example, 1.0 kgf (9.8 N). Note that, because the arm total weight counterbalances to the biasing force applied to the multijoint arm 3 and the working portion 5, the measured force data sent from the force sensor 45 shows zero.

Following the first action, the doctor performs the second action to positively apply force to the arm holder 51 of the working portion 5 via the right arm A downward in order to make the working portion 5 follow movement of the right arm A. Because the applied force is to positively move the working portion 5, the applied force is normally equal to or greater than the threshold level F1. For example, in the first embodiment, the threshold level F1 is set to 1.5 kgf (14.7 N) corresponding to the total arm weight. In the first embodiment, the relationship between the first threshold level F1, the second threshold level F2, and the total arm weight, referred to TW, preferably meets the following equation:

$$TW \geq F1 > F2$$

Specifically, in step S2, the CPU 7 determines, based on the measured force data and torque data sent from the force sensor 45, whether:

force applied to the arm holder 51 of the working portion 5, i.e. the working end 51GE of the second guide part 51G2, has been equal to or greater than the first threshold level F1 for 100 ms; or:

torque applied to the arm holder 51 has been equal to or greater than first threshold level Tr1 equal to 10 kg·cm (98 N·cm) for 100 ins; the first threshold level Tr1 corresponds to the first threshold level F1.

Note that the condition whether force applied to the arm holder 51 of the working portion 5 has been equal to or greater than the first threshold level F1 for 100 ms will be referred to as a first condition. Similarly, the condition whether torque applied to the arm holder 51 has been equal to or greater than the first threshold level Tr1 equal to 98 N·cm for 100 ms will be referred to as a second condition.

Upon determination that neither the first condition nor the second condition is satisfied (NO in step S2), the CPU 71 repeats the determination in step S2, thus maintaining the operation mode of the body support apparatus 1 in the wait mode.

Otherwise, upon determination that at least one of the first condition and the second condition is satisfied, the CPU 71 determines that the doctor tries to move the right arm A to cause the working portion 5 to follow movement of the right arm A based on the measured force and torque data (YES in step S2).

Then, the CPU 71 sets the operation mode of the body support apparatus 1 to a free mode in step S3. Specifically, the free mode is designed assuming that a doctor tries to make the working portion 5 follow movement of the right arm A. That is, in the free mode, the CPU 71 deactivates the brakes 31A, 32A, and 33A to allow movement of the corresponding joints 31, 32, and 33, respectively in step S3a. In addition, in step S3b, the CPU 71 turns on the drivers 79, thus energizing the electromagnets 52a and 52b. In step S2c, the CPU 71 instructs each of the first and second light sources 58 and 59 to cause orange light to flash.

Specifically, in the free mode, when the doctor moves the right arm A, the working portion 5 follows the movement of the right arm A because the joints 31 to 35 can move freely and the right arm A is fixedly supported on the arm holder 51 based on the electromagnets 52a and 52b and the magnetic plates 57a and 57b. In addition, as described above, because force applied from the working portion 5 to the right arm A is very weak force, and slide resistance of each of the brakes 31A, 32A, and 33A, the doctor can easily move the working portion 5 to follow movement of the right arm A using weak force applied to the working portion 5.

The flashing orange light emitted from the first light source 58 permits the doctor to easily know that the operating mode of the body support apparatus 1 is set in the free mode.

Specifically, even if the doctor is performing surgical operations to the affected site of the patient using a surgical operation tool held by the right hand, it is possible for the doctor to easily know that the operating mode of the body support apparatus 1 is set in the free mode. This is because the first light source 58 is located in the peripheral visual field PVF while the doctor is looking at the affected site so that the center visual field CVF is located on the affected site.

In addition, the flickered orange light emitted from the second light source 59 permits one or more assistants to easily know that the operating mode of the body support apparatus 1 is set in the free mode.

Next, the CPU 71 determines whether the doctor tries to finish movement of the working portion 5 at a desired position to thereby fix the working portion 5 to the corresponding position based on the measured amount of rotation sent from each of the encoders 31B to 33B in step S4.

Specifically, in step S4, the CPU 7 determines, based on the measured amount of rotation sent from each of the encoders 31B to 33B, whether the movement speed of the working portion 5, i.e. the working end 51GE of the second guide part 51G2, has been equal to or lower than a preset threshold level V of, for example, 1 mm/s for 100 ms.

Upon determination that the movement speed of the working portion 5 has been greater than the preset threshold level V for 100 ms (NO in step S4), the CPU 71 repeats the determination in step S4, thus maintaining the operation mode of the body support apparatus 1 in the free mode.

Otherwise, upon determination that the movement speed of the working portion 5 has been equal to or lower than the preset threshold level V for 100 ms (YES in step S4), the CPU 71 determines that the doctor tries to finish movement of the working portion 5 at a desired position to thereby fix the working portion 5 to the corresponding position.

Then, the CPU 71 sets the operation mode of the body support apparatus 1 to a lock mode in step S5. Specifically, the lock mode is designed assuming that a doctor tries to perform surgical operations using the right arm A while the right arm A is free from the arm holder 51 of the working portion 5.

That is, in the lock mode, the CPU 71 activates the brakes 31A, 32A, and 33A to stop movement of the corresponding joints 31, 32, and 33, respectively in step S5a. In addition, in step S5b, the CPU 71 turns off the drivers 79, thus deenergizing the electromagnets 52a and 52b. In step S5c, the CPU 71 instructs each of the first and second light sources 58 and 59 to emit continuous blue light.

Specifically, in the lock mode, the doctor can perform fine surgical operations to the affected site using the right arm A while moving the right arm A freely from the working portion 5. The blue light emitted from the first light source 58 permits the doctor to easily know that the operating mode of the body support apparatus 1 is set in the lock mode.

Specifically, even if the doctor is performing surgical operations to the affected site of the patient using a surgical operation tool held by the right hand, it is possible for the doctor to easily know that the operating mode of the body support apparatus 1 is set in the lock mode. This is because the first light source 58 is located in the peripheral visual field PVF while the doctor is looking at the affected site so that the center visual field CVF is located on the affected site.

In addition, the blue light emitted from the second light source 59 permits one or more assistants to easily know that the operating mode of the body support apparatus 1 is set in the lock mode.

Next, the CPU 71 determines whether the doctor tries to shift the operation mode of the body support apparatus 1 from the lock mode to the wait mode based on the measured force and torque data in step S6.

Specifically, in step S6, the CPU 7 determines, based on the measured force data and torque data sent from the force sensor 45, whether:

force applied to the arm holder 51 of the working portion 5, i.e. the working end 51GE of the second guide part 51G2, has been equal to or smaller than the second threshold level F2 for 200 ms; or:

torque applied to the arm holder 51 has been equal to or smaller than second threshold level Tr2 equal to 5 kg·cm (49 N·cm) for 200 ms; the second threshold level Tr2 corresponds to the second threshold level F2.

Note that the condition whether force applied to the arm holder 51 of the working portion 5, i.e. the working end 51GE of the second guide part 51G2, has been equal to or smaller than the second threshold level F2 for 200 ms will be referred to as a third condition. Similarly, the condition whether torque applied to the arm holder 51 has been equal to or smaller than the second threshold level Tr2 equal to 49 N·cm for 200 ms will be referred to as a fourth condition.

Upon determination that neither the third condition nor the fourth condition is satisfied (NO in step S6), the CPU 71 repeats the determination in step S6, thus maintaining the operation mode of the body support apparatus 1 in the lock mode.

Otherwise, upon determination that at least one of the third condition and the fourth condition is satisfied, the CPU 71 determines that the doctor tries to shift the operation mode of the body support apparatus 1 from the lock mode to the wait mode (YES in step S6).

Then, the CPU 71 carries out the operation in step S1, thus shifting the operation mode of the body support apparatus 1 from the lock mode to the wait mode (see step S1).

As described above, the determination that force applied to the working portion 5 has been equal to or smaller than the second threshold level F2 for 200 ms shows one of:

a first state in which the doctor performs the first action to support the right arm A with the muscle of the right arm A; and a second state in which the doctor tries to remove the right area A from the arm holder 51 of the working portion 5. In the first state, after execution of the operation in step S1, the CPU 71 performs the operation in step S2, and immediately performs an affirmative determination in step S2 set forth above, thus carrying out the next operation in step S3.

However, in the second state, after execution of the operation in step S1, the CPU 71 performs the operation in step S2, and repeatedly performs a negative determination in step S2, so that the operation mode of the body support apparatus 1 is maintained in the wait mode.

Next, how the operation mode of the body support apparatus 1 is shifted based on execution of the mode determination task will be described hereinafter with reference to FIG. 5.

While the operation mode of the body support apparatus 1 is set to the wait mode (see step S1), the brakes 31A to 33A are operating to brake the corresponding joints 31 to 33, the electromagnets 52a and 52b are deenergized, and continuous orange light is output from each of the first and second light sources 58 and 59 (see steps S1a to S1c).

Figure 5:
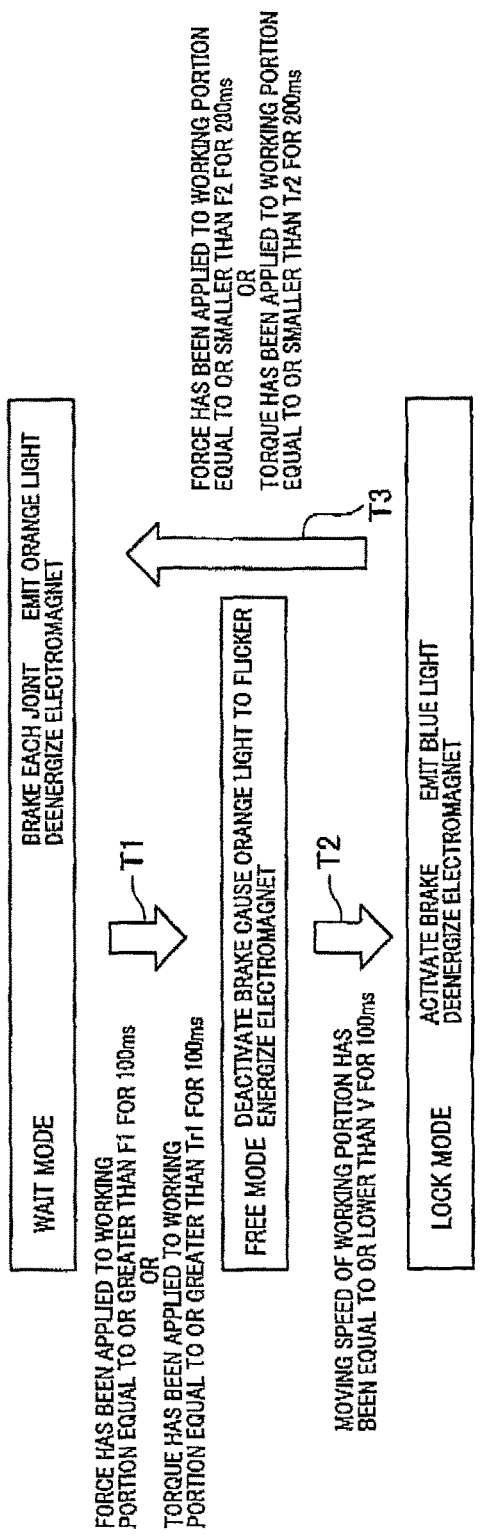
FIG. 5 is a mode transition view schematically illustrating how an operation mode of the body support apparatus changes according to the first embodiment.

During the wait mode of the body support apparatus 1, when force applied to the arm holder 51 of the working portion 5 has been equal to or greater than the first threshold level F1 for 100 ms or torque applied to the arm holder 51 has been equal to or greater than the first threshold level Tr1 equal to 98 N·cm for 100 ms (YES in step S2), the operation mode of the body support apparatus 1 is shifted from the wait mode to the free mode (see step S3 in FIG. 4 and T1 in FIG. 5).

While the operation mode of the body support apparatus 1 is set to the free mode, the brakes 31A to 33A are deactivated to allow movement of the corresponding joints 31 to 33, the electromagnets 52a and 52b are being energized to fixedly support the right arm A on the arm holder 51 of the working portion 5, and flickered orange light is output from each of the first and second light sources 58 and 59 (see steps S3a to S3c).

During the free mode of the body support apparatus 1, when the movement speed of the working portion 5 has been equal to or lower than the preset threshold level V for 100 ms (YES in step S4), the operation mode of the body support apparatus 1 is shifted from the free mode to the lock mode (see step S5 in FIG. 4 and T2 in FIG. 5).

While the operation mode of the body support apparatus 1 is set to the lock mode (see step S5), the brakes 31A to 33A are operating to brake the corresponding joints 31 to 33, the electromagnets 52a and 52b are being deenergized, and continuous blue light is output from each of the first and second light sources 58 and 59 (see steps S5a to S5c).

During the lock mode of the body support apparatus 1, when force applied to the arm holder 51 of the working portion 5 has been equal to or greater than the second threshold level F2 for 200 ms or torque applied to the arm holder 51 has been equal to or greater than the second threshold level Tr2 equal to 49 N·cm for 200 ms (YES in step S6), the operation mode of the body support apparatus 1 is shifted from the lock mode to the wait mode (see steps S6 and S1 in FIG. 4 and T3 in FIG. 5).

Accordingly, the body support apparatus 1 according to the first embodiment makes it possible to repeatedly shift the operation mode thereof among the wait mode, the free mode, and the lock mode in the following order of the wait mode, the free mode, and the lock mode. Thus, there is no need to operate switches or other devices to change the operation mode of the body support apparatus 1, thus allowing the doctor to smoothly perform surgical operations to the affected site. Because the operation mode of the body support apparatus 1 is repeatedly changed in the predetermined sequential order of the wait mode, the free mode, and the lock mode, it is possible for the doctor to intuitively understand that the operation mode of the body support apparatus 1 is set to which of the aforementioned three modes, thus minimizing erroneous operations of the body support apparatus 1.

In addition, the configuration of the body support apparatus 1 permits addition of weak force to the right arm A to make the working portion 5 follow movement of the right arm A, and permits the right arm A to be easily attached to and removed from the working portion 5. This therefore improves the doctor's operability of the body support apparatus 1.

Moreover, in the body support apparatus 1, the first light source 58 has a special positional relationship with respect to the peripheral visual field PVF of the doctor with the right arm A being supported on the arm holder 51 such that the first light source 58 is located within the peripheral visual field PVF. Specifically, in the first embodiment, the first light source 58 is mounted on the left-side of the working end of the second guide part 51G2 in the front direction of the supporting base 41 M (see FIG. 2B). This arrangement of the first light source 58 makes possible that the first light source 58 is located in a right-edge of the peripheral visual field PVF.

Thus, even if the doctor is performing surgical operations to the affected site of the patient using a surgical operation tool held by the right hand, the doctor easily recognizes how the first light source 58 emits colored light. This permits the doctor to easily check the current operating mode of the body support apparatus 1 while performing surgical operations to the affected site of the patient without looking aside from the affected sight. This makes it possible for the doctor to successfully concentrate on the surgical operations at the affected site.

In addition, in the body support apparatus 1, the second light source 59 is mounted on the right-side of the working end 51GE of the second guide part 51G2 in front direction of the supporting base 41 while it is viewed from the doctor who is seated on the chair 6. Specifically, because the doctor is positioned at the left side of the supporting base 41, one or more assistants, who assist the doctor, are normally positioned at the right side of the supporting base 41. Thus, it is possible for one or more assistants to easily recognize how the second light source 59 emits light, thus easily checking the current operation mode of the body support apparatus 1. This effectively prevents one or more assistants from erroneously touching the working portion 5 whose position is not completely fixed, thus further improving the assistant's concentration when working.

Preferably, the second light source 59 is mounted on the right-side of the working end 51GE of the second guide part 51G2 in the front direction of the supporting base 41 M. This arrangement of the second light source 59 makes possible that the second light source 59 is located out of the peripheral visual field PVF. This can prevent the second light source 59 from disturbing the doctor who is performing surgical operations.

Second Embodiment

Figure 6:
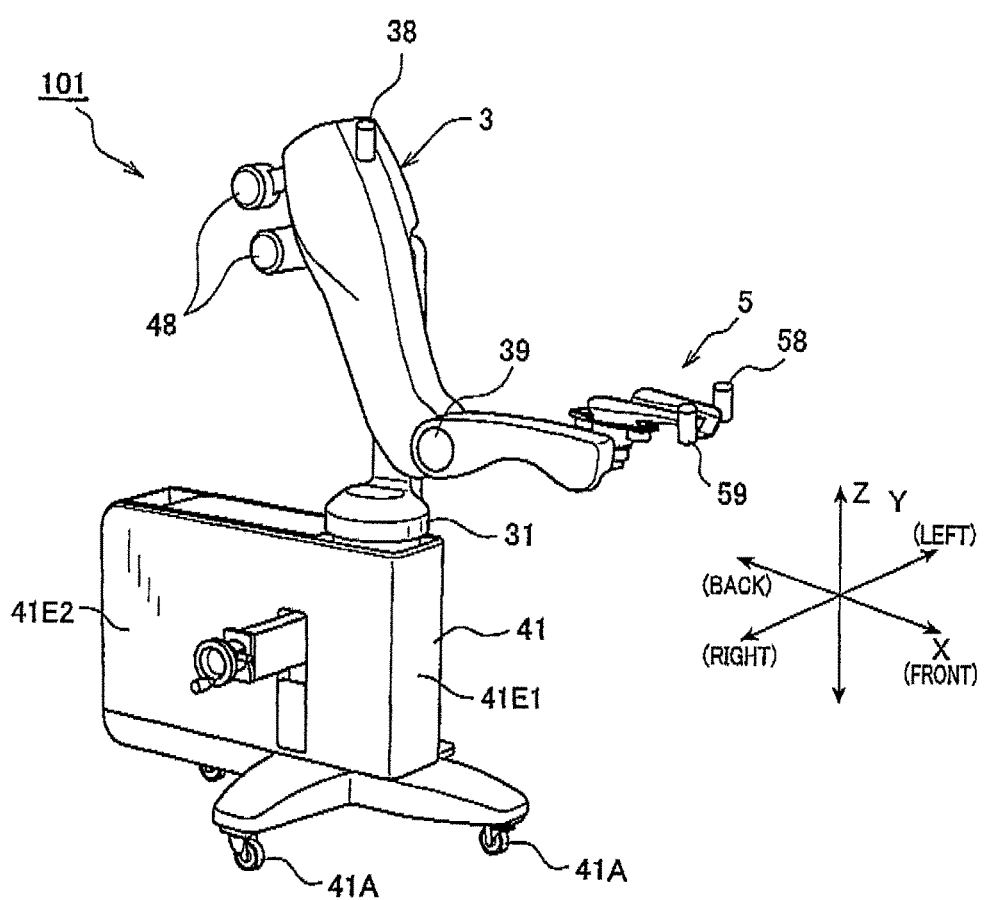
FIG. 6 is a perspective view schematically illustrating the outward appearance of a body support apparatus and an operation-mode indicating system according to the second embodiment of the present disclosure.

A body support apparatus 101 according to the second embodiment of the present disclosure will be described hereinafter with reference to FIG. 6.

The structure and/or functions of the body support apparatus 101 according to the second embodiment are different from those of the body support apparatus 1 by the following points. So, the different points will be mainly described hereinafter, and therefore, redundant descriptions of like parts between the embodiments, to which like reference characters are assigned, are omitted or simplified.

In the first embodiment, how each of the first and second light sources 58 and 59 is located in the body support apparatus 1, and how many first and second light sources 58 and 59 are located in the body support apparatus 1, are limited to the configuration of the first embodiment.

Specifically, the body support apparatus 101 according to the second embodiment is equipped with, in addition to the second light source 59 mainly for assistants, a third light source 38 and a fourth light source 39 mainly for assistants. For example, referring to FIG. 6, the third light source 38 is attached to a top portion of the first arm member 43 of the multijoint arm 3, and the fourth light source 39 is attached to the right side of the first end of the second arm member 44.

Other structures and functions of the body support apparatus 101 are substantially identical to those of the body support apparatus 1, so descriptions of which are omitted.

Specifically, because the third light source 38 is attached to the top portion of the first arm member 43 of the multijoint arm 3, one or more assistants, who are positioned at the right arm 3, can easily recognize how the third light source 38 emits light. Similarly, because the fourth light source 39 is attached to the right side of the first end of the second arm member 44, one or more assistants, who are positioned at the right side of the supporting base 41, can easily recognize how the fourth light source 39 emits light. Thus, it is possible for one or more assistants to more easily check the current operation mode of the body support apparatus 101. In addition, each of the third and fourth light sources 38 and 39 is located out of the peripheral visual field PVF. This can prevent the third and fourth light sources 38 and 39 from disturbing the doctor who is performing surgical operations.

Third Embodiment

A body support system 201 according to the third embodiment of the present disclosure will be described hereinafter with reference to FIGS. 7 and 8A to 8C.

The structure and/or functions of the body support system 201 according to the third embodiment are different from those of the body support apparatus 1 by the following points. So, the different points will be mainly described hereinafter, and therefore, redundant descriptions of like parts between the embodiments, to which like reference characters are assigned, are omitted or simplified.

Figure 7:
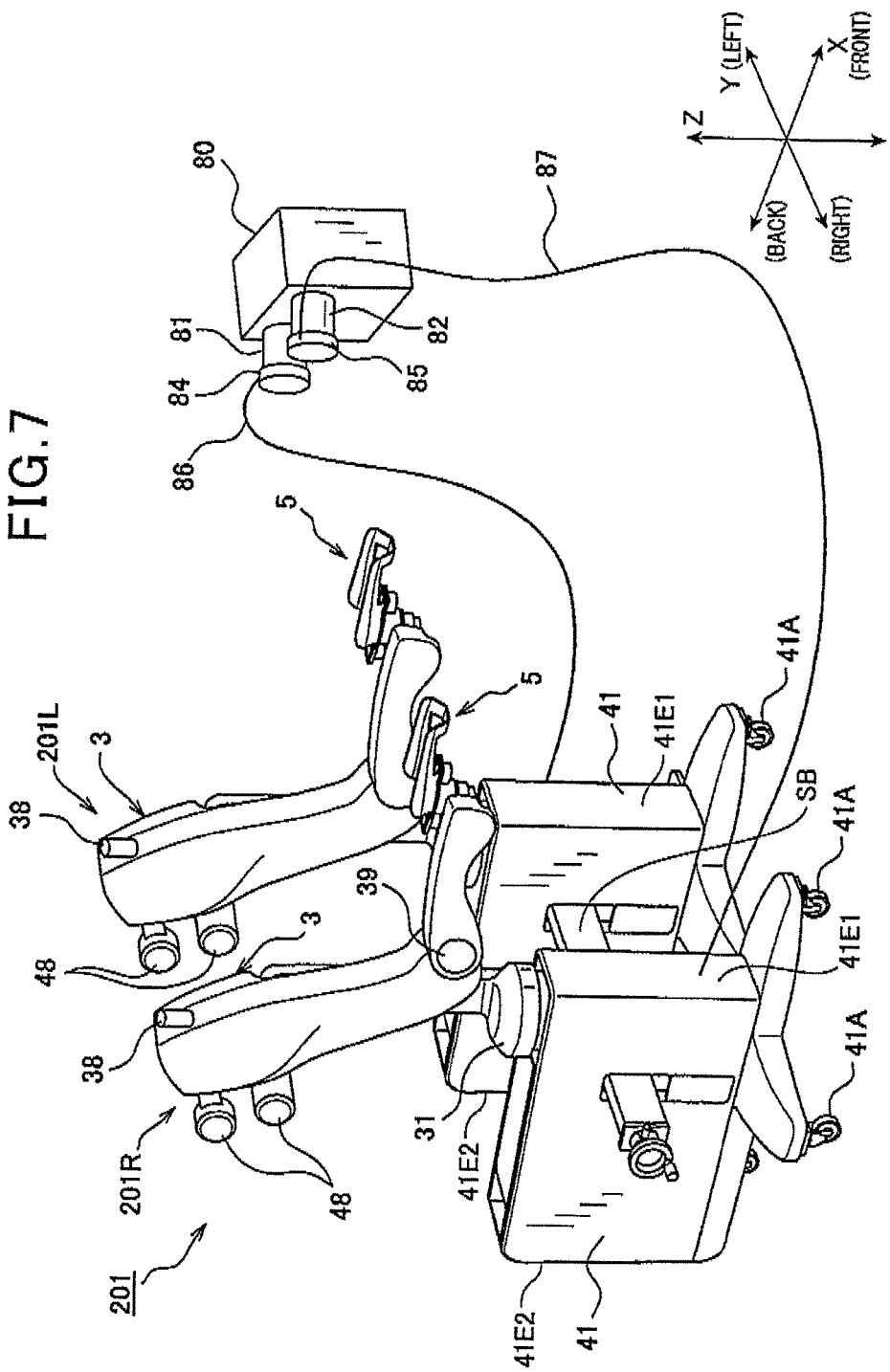
FIG. 7 is a perspective view schematically illustrating the outward appearance of a body support apparatus and an operation-mode indicating system according to the third embodiment of the present disclosure.

Referring to FIG. 7, the body support system 201 is equipped with a first body support apparatus 201L for the left hand of a doctor, and a second body support apparatus 201R for the right hand of, for example, the same doctor.

Each of the first and second body support apparatuses 201L and 201R has a substantially identical configuration to that of the body support apparatus 1 except for light sources. The first and second body support apparatuses 201L and 201R are arranged on the floor FL such that the right-side surface of the supporting base 41 of the first body support apparatus 201L faces the left-side surface of the supporting base 41 of the second body support apparatus 201B. The front-side surface of the supporting base 41 of the first body support apparatus 201L and that of the supporting base 41 of the second body support apparatus 201R are aligned with each other in the Y direction. The supporting base 41 of the first body support apparatus 201L and that of the second body support apparatus 201R are, for example, joined to each other via a support bar SB.

Although the chair 6 is not illustrated in FIG. 7, a chair is located in front of the support bar SB close to the front side of the first body support apparatus 201L and that of the second body support apparatus 201R. Specifically, a doctor, who is seated on the chair and is going to perform surgical operations using both the apparatuses 201L and 201R, can mount the right hand on the arm holder 51 of the working portion 5 of the second body support apparatus 201R, and mount the left hand on the arm holder 51 of the working portion 5 of the first body support apparatus 201L. The first body support apparatus 201L can be used for the right hand of another doctor.

As illustrated in FIG. 7, the second body support apparatus 201R is equipped with, in place of the first and second light sources 58 and 59, the third and fourth light sources 38 and 39 like the second embodiment. Specifically, the third light source 38 is attached to the top portion of the first arm member 43 of the multijoint arm 3, and the fourth light source 39 is attached to the right side of the first end of the second arm member 44.

Similarly, the first body support apparatus 201L is equipped with, in place of the first and second light sources 58 and 59, the third light source 38 and a fifth light source (not shown) like the second embodiment. Specifically, the third light source 38 is attached to the top portion of the first arm member 43 of the multijoint arm 3, and the fifth light source is attached to the left side of the first end of the second arm member 44.

In addition, FIG. 7 schematically illustrates a binocular surgical microscope 80 equipped with a cylindrically-shaped left eyepiece 81 for left eyes and a cylindrically-shaped right eyepiece 82 for right eyes. The left and right eyepieces 81 and 82 are located close to the body support system 201 and side-by-side in the horizontal direction parallel to the floor FL. Specifically, the doctor, who is seated on the chair, is going to look through the left and right eyepieces 81 and 82 in order to perform surgical operations. Thus, the left eyepiece 81 corresponds to the center visual field of the left eye of the doctor, and the right eyepiece 82 corresponds to the center visual field of the right eye of the doctor according to the third embodiment.

The first body support apparatus 201L is also equipped with a first light source 84 for doctors, and the second body support apparatus 201R is also equipped with a first light source 85 for doctors.

Figure 8A:
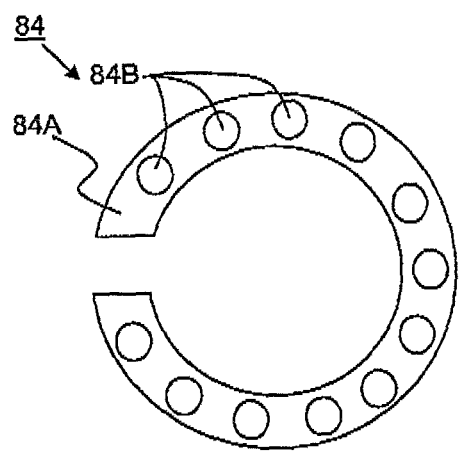
FIG. 8A is a view schematically illustrating a first light source according to the third embodiment.

As illustrated in FIG. 8A, the first light source 84 is comprised of a substantially ring-shaped holder 84A having a gap. The holder 84A is flexible, so that it can be removably fitted around one end of the left eyepiece 81. The first light source 84 is comprised of a plurality of LEDs 843 mounted on an end surface of the frame 84A at regular intervals. Each of the LEDs 843 is electrically connected to the controller 7 via signal a signal line 86. Under control of the controller 7 installed in the supporting base 41, each of the LEDs 843 is capable of normally emitting different colors of light, and causing a selected color of light to flash.

The first light source 85 has the same structure as that of the first light source 84, and therefore, the descriptions of which are omitted. Reference numeral 87 shows signal lines through which each LED of the first light source 85 is electrically connected to the controller 7 installed in the supporting base 41.

Figure 8B:
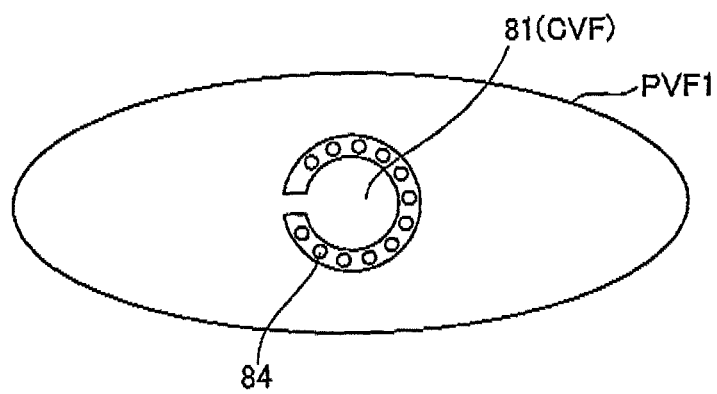
FIG. 8B is a view schematically illustrating a positional relationship between a peripheral visual field of the doctor, which is defined around a left eyepiece, and the first light source according to the third embodiment.
Figure 8C:
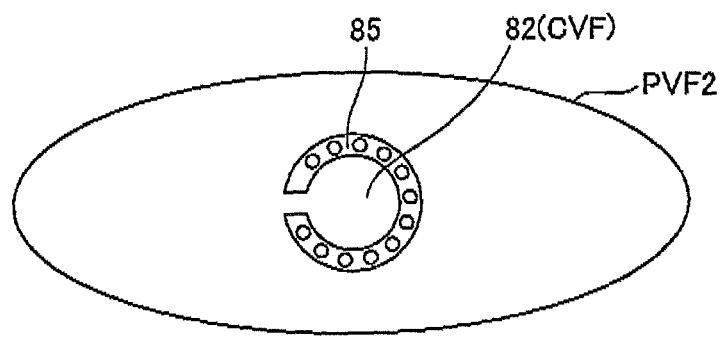
FIG. 8C is a view schematically illustrating a positional relationship between a peripheral visual field of the doctor, which is defined around a right eyepiece, and the first light source according to the third embodiment.

Specifically, because the LEDs 843 of the first light source 84 are arranged around the left eyepiece 81 corresponding to the center visual field CVF of the left eye of the doctor, the LEDs 843 are located in a peripheral visual field PVF1 of the doctor defined around the left eyepiece 81 (see FIG. 8B). Similarly, because the LEDs of the first light source 85 are arranged around the right eyepiece 82 corresponding to the center visual field CVF of the right eye of the doctor, the LEDs are located in a peripheral visual field PVF2 of the doctor defined around the right eyepiece 81 (see FIG. 8C).

Like the first embodiment, the controller 7 is programmed to perform the mode determination task illustrated in FIG. 4 for each of the first body support apparatus 201L and the second body support apparatus 201R.

Other structures and functions of the body support system 201 are substantially identical to those of the body support apparatus 1, so descriptions of which are omitted.

In the body support system 201 according to the third embodiment, the LEDs 84 of the first light source 84 are located in the peripheral visual field PVF1 of the left eye of the doctor. Similarly, the LEDs of the first light source 85 are located in the peripheral visual field PVF2 of the right eye of the doctor.

Thus, even if the doctor is performing surgical operations on the affected site of the patient using surgical operation tools held by both the right hand and left hand, the doctor easily recognizes how each of the first light sources 84 and 85 emits colored light via a corresponding one of the left and right eyes. This permits the doctor to easily check the current operating mode of each of the first and second body support apparatuses 201L and 201R while performing surgical operations to the affected site of the patient without looking aside from the affected sight. This makes it possible for the doctor to successfully concentrate on the surgical operations at the affected site.

Note that the first light sources 84 and 85 can be installed in the respective left and right eyepieces 81 and 82. As described above, the first light sources 84 and 85, which are removably fitted around the respective left and right eyepieces 81 and 82, make it possible to use a normally available binocular surgical microscope in combination of the first light sources 84 and 85.

In addition, in the body support system 201, even if a doctor, who is mounting both left and right arms on the working portions 5 of the respective apparatuses 201L and 201R, is looking up at the left and right eyepieces 81 and 82, it is possible for such a doctor to easily recognize how each of the first light sources 84 and 85 emits colored light via a corresponding one of the left and right eyes.

Fourth Embodiment

A body support apparatus 301 according to the fourth embodiment of the present disclosure will be described hereinafter with reference to FIGS. 9 to 11.

The structure and/or functions of the body support apparatus 301 according to the fourth embodiment are different from those of the body support apparatus 1 by the following points. So, the different points will be mainly described hereinafter, and therefore, redundant descriptions of like parts between the embodiments, to which like reference characters are assigned, are omitted or simplified.

The body support apparatus 1 according to the first embodiment is configured to determine a timing to change the operation mode thereof to another according to the measured force data and torque data, but the present disclosure is not limited thereto. Specifically, each of the body support apparatuses 1, 101, 201R, and 201L can be configured to determine a timing to change the operation mode thereof to another using another measure.

Figure 9:
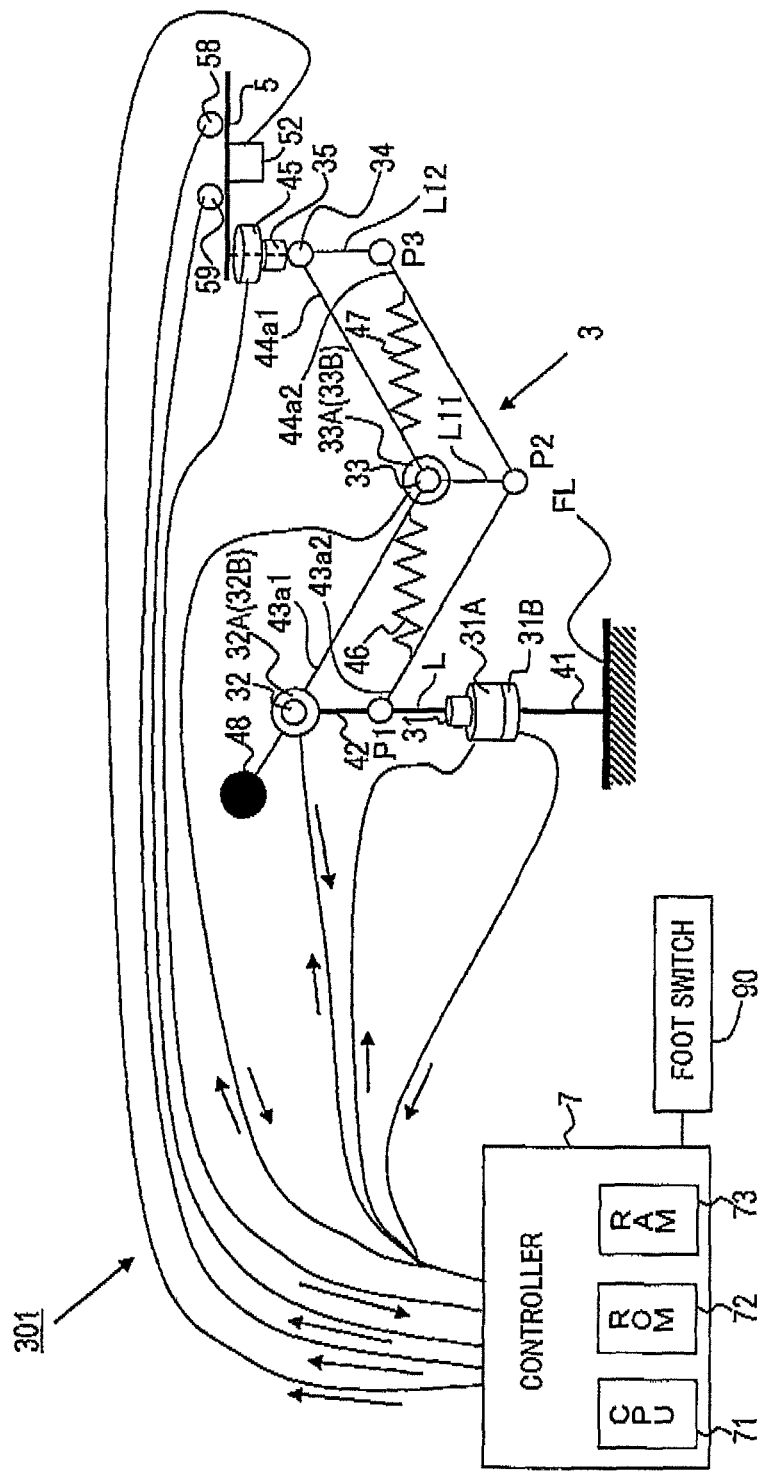
FIG. 9 is a schematic view of a body support apparatus and an operation-mode indicating system according to the fourth embodiment of the present disclosure.

FIG. 9 illustrates a schematic view of the body support apparatus 301 according to the fourth embodiment of the present disclosure. The body support apparatus 301 is further equipped with a foot switch 90 electrically connected to the controller 7. The foot switch 90 is capable of sending an instruction to the controller 7 each time the doctor, whose right arm A is mounted on the arm holder 51 of the working portion 5, depresses the foot switch 90 using a foot. Note that one of various switches operable by the doctor, whose right arm A is mounted on the arm holder 51 of the working portion 5, can be used in place of the foot switch 90.

Figure 10:
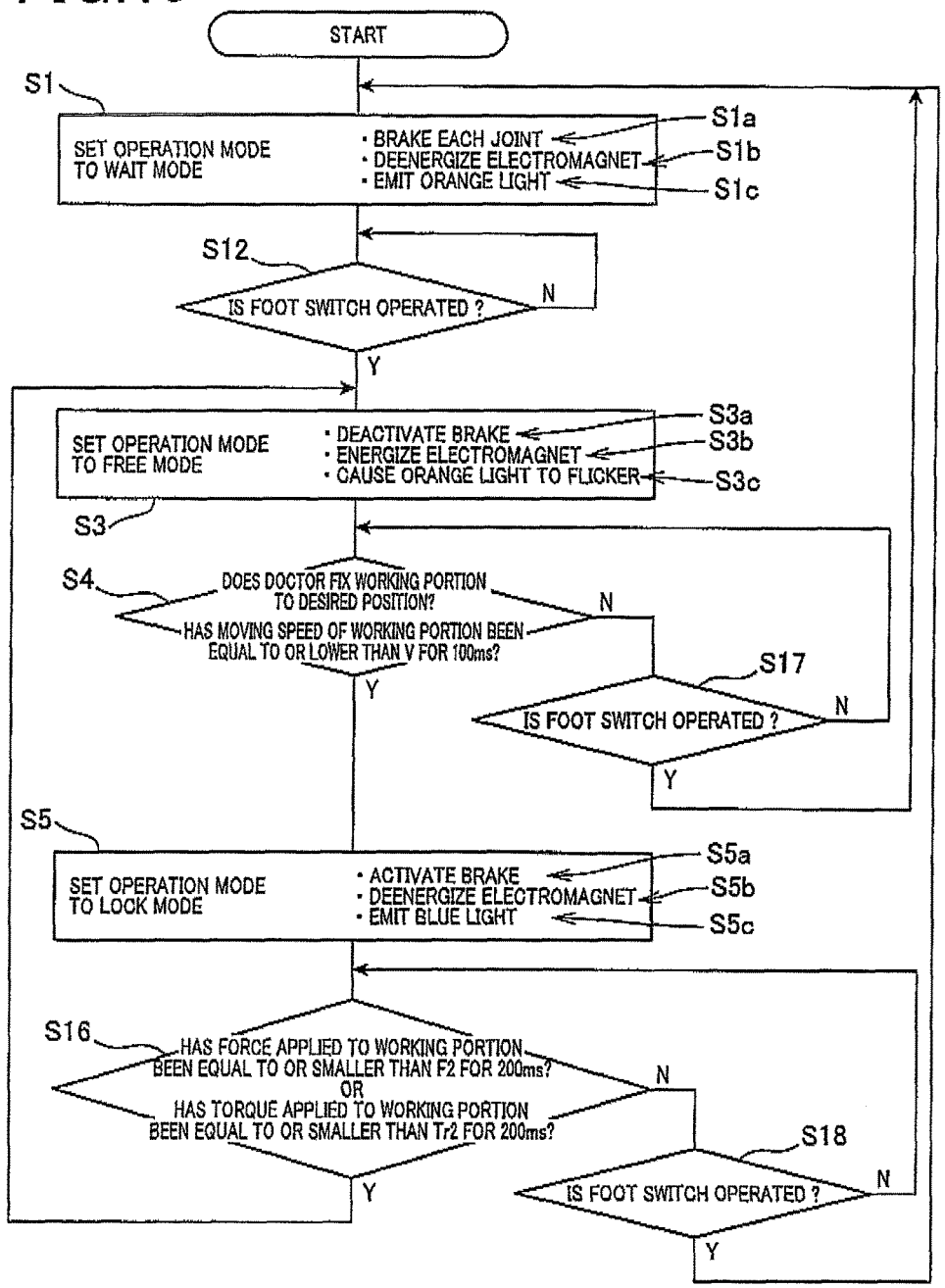
FIG. 10 is a flowchart schematically illustrating a mode determination task carried out by a controller illustrated in FIG. 9.

The controller 7 is programmed to perform a mode determination task illustrated in FIG. 10. In the flowchart illustrated in FIG. 10, like steps to the flowchart illustrated in FIG. 4, to which like step numbers are assigned, are omitted or simplified to avoid redundant description.

When starting the mode determination task illustrated in FIG. 10, the CPU 71 performs the operation in step S1 to thereby set the operation mode of the body support apparatus 301 to the wait mode in step S1.

During the wait mode, the CPU 71 determines whether the foot switch 90 is operated by the doctor in step S12.

Upon determination that the foot switch 90 is not operated by the doctor (NO in step S12), the CPU 71 repeats the determination in step S2, thus maintaining the operation mode of the body support apparatus 301 in the wait mode.

Otherwise, upon determination that the foot switch 90 is operated by the doctor (YES in step S12), the CPU 71 determines that the doctor tries to move the right arm A to cause the working portion 5 to follow movement of the right arm A.

Then, the CPU 71 sets the operation mode of the body support apparatus 301 to the free mode in step S3.

Next, the CPU 71 determines, based on the measured amount of rotation sent from each of the encoders 31B to 33B, whether the movement speed of the working portion 5, i.e. the working end 51GE of the second guide part 51G2, has been equal to or lower than the preset threshold level V of, for example, 1 mm/s for 100 ms in step S4.

Upon determination that the movement speed of the working portion 5 has greater than the preset threshold level V for 100 ms (NO in step S4), the CPU 71 determines whether the foot switch 90 is operated by the doctor in step S17. Upon determination that the foot switch 90 is not operated by the doctor (NO in step S17), the CPU 71 repeats the determination in step S4, thus maintaining the operation mode of the body support apparatus 1 in the free mode. Otherwise, upon determination that the foot switch 90 is operated by the doctor (YES in step S17), the CPU 71 carries out the operation in step S1, thus setting the operation mode of the body support apparatus 301 to the wait mode (see step S1).

Specifically, during the free mode, the CPU 71 determines whether the movement speed of the working portion 5 has been equal to or lower than the preset threshold level V for 100 ms (see step S4), and determines whether the foot switch 90 is operated by the doctor until the movement speed of the working portion 5 has been equal to or greater than the preset threshold level V for 100 ms (see step S17).

Otherwise, upon determination that the movement speed of the working portion 5 has been equal to or lower than the preset threshold level V for 100 ms without operation of the foot switch 90 (YES in step S4 and NO in step S17), the CPU 71 determines that the doctor tries to finish movement of the working portion 5 at a desired position to thereby fix the working portion 5 to the corresponding position.

Then, the CPU 71 sets the operation mode of the body support apparatus 301 to the lock mode in step S5.

Next, in step S16, the CPU 71 determines, based on the measured force data and torque data sent from the force sensor 45, whether:

force applied to the arm holder 51 of the working portion 5 has been equal to or smaller than the second threshold level F2 for 200 ms; or:

torque applied to the arm holder 51 has been equal to or smaller than second threshold level Tr2 for 200 ms.

Upon determination that at least one of the third condition and the fourth condition is satisfied, the CPU 71 determines that the doctor tries to shift the operation mode of the body support apparatus 1 from the lock mode to the free mode (YES in step S16). Then, the CPU 71 carries out the operation in step S3 to thereby set the operation mode of the body support apparatus 301 to the free mode.

Specifically, the determination that force applied to the working portion 5 is equal to or smaller than the threshold level F2 shows a state in which the doctor performs the first action to support the right arm A with the muscle of the right arm A. In the fourth embodiment, when it is determined that this state has been continued for 200 ms (YES in step S16), the operation mode of the body support apparatus 301 is set to the free mode (see step S3).

Otherwise, upon determination that neither the third condition nor the fourth condition is satisfied (NO in step S16), the CPU 71 determines whether the foot switch 90 is operated by the doctor in step S18. Upon determination that the foot switch 90 is not operated by the doctor (NO in step S18), the CPU 71 repeats the determination in step S16, thus maintaining the operation mode of the body support apparatus 1 in the lock mode. Otherwise, upon determination that the foot switch 90 is operated by the doctor (YES in step S18), the CPU 71 carries out the operation in step S1, thus setting the operation mode of the body support apparatus 301 to the wait mode (see step S1).

Specifically, during the free mode, the CPU 71 determines whether at least one of the third condition and the fourth condition is met (see step S16), and determines whether the foot switch 90 is operated by the doctor until at least one of the third condition and the fourth condition is met (see step S18).

Next, how the operation mode of the body support apparatus 301 is shifted based on execution of the mode determination task will be described hereinafter with reference to FIG. 11.

Figure 11:
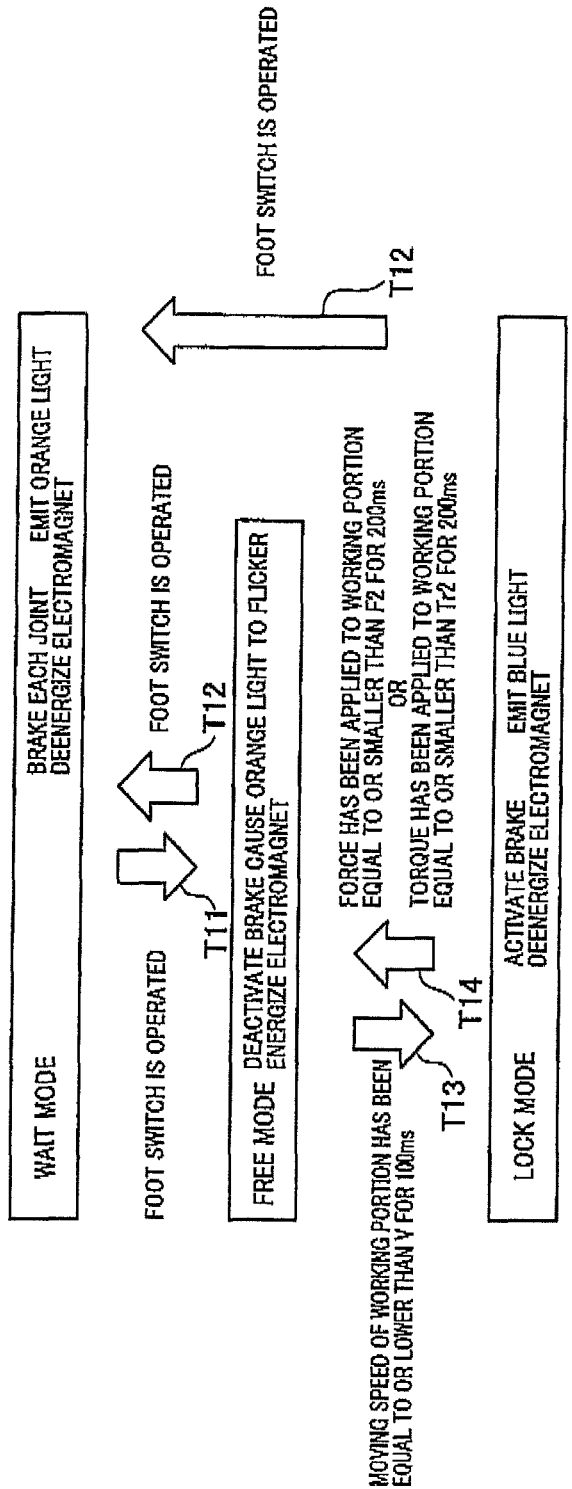
FIG. 11 is a mode transition view schematically illustrating how an operation mode of the body support apparatus changes according to the fourth embodiment.

While the operation mode of the body support apparatus 1 is set to the wait mode (see step S1), when the foot switch 90 is operated by the doctor (YES in step S12), the operation mode of the body support apparatus 301 is shifted from the wait mode to the free mode (see step S3 in FIG. 10 and T11 in FIG. 11). At that time, flickered orange light is output from each of the first and second light sources 58 and 59 (see step S3). In addition, while the operation mode of body support apparatus 1 is set to the free mode (see step S3) or the lock mode (see step S5), when the foot switch 90 is operated by the doctor (YES in step S17 or YES in step S18), the operation mode of the body support apparatus 301 is shifted to the wait mode (see T12 in FIG. 11).

While the operation mode of body support apparatus 1 is set to the free mode (see step S3), when the movement speed of the working portion 5 has been equal to or lower than the preset threshold level V for 100 ms (YES in step S4), the operation mode of the body support apparatus 301 is shifted from the free mode to the lock mode (see step S5 in FIG. 10 and T13 in FIG. 11). At that time, blue light is continuously output from each of the first and second light sources 58 and 59 (see step S5). During the lock mode, when force applied to the arm holder 51 of the working portion 5 has been equal to or smaller than the second threshold level F2 for 200 ms, or torque applied to the at holder 51 has been equal to or smaller than second threshold level Tr2 for 200 ms (YES in step S16), the operation mode of the body support apparatus 301 is shifted from the lock mode to the free mode (see step S3 in FIG. 10 and T14 in FIG. 11).

Accordingly, the body support apparatus 301 according to the fourth embodiment is configured to automatically shift the operation mode thereof between the free mode and the lock mode based on: a first parameter indicative of how force and/or torque has been applied to the working portion 5, and a second parameter indicative of how the working portion 5 is moved. This therefore makes it possible for the doctor to smoothly perform surgical operations.

In addition, the body support apparatus 301 is configured to shift the operation mode thereof between the wait mode and one of the free mode and the lock mode according to whether the foot switch 90 is operated by the doctor. This configuration makes it possible to reliably shift the operation mode of the body support apparatus 301 to the wait mode by manual operation of the foot switch 90 when:

the doctor wants not to cause the working portion 5 to follow movement of the right arm A in order to, for example, take a surgical operation tool; or the doctor wants absolutely not to move the working portion 5 in order to perform particularly important operations using the right hand.

In addition, after the operation mode of the body support apparatus 301 has been shifted to the wait mode, it is possible to reliably maintain the operation mode of the body support apparatus 301 in the wait mode until next operation of the foot switch 90. This gives secure feeling to the doctor. Note that, in the fourth embodiment, during the wait mode, when the foot switch 90 is operated by the doctor, the operation mode can be shifted from the wait mode to the lock mode.

Fifth Embodiment

A body support apparatus according to the fifth embodiment of the present disclosure will be described hereinafter with reference to FIGS. 12 and 13.

The structure and/or functions of the body support apparatus according to the fifth embodiment are different from those of the body support apparatus 1 by the following points. So, the different points will be mainly described hereinafter, and therefore, redundant descriptions of like parts between the embodiments, to which like reference characters are assigned, are omitted or simplified.

The controller 7 of the body support apparatus according to the fifth embodiment is programmed to perform a mode determination task illustrated in FIG. 12. In the flowchart illustrated in FIG. 12, like steps to the flowchart illustrated in FIG. 4, to which like step numbers are assigned, are omitted or simplified to avoid redundant description.

In the fifth embodiment, a threshold level for force applied to the arm holder 51 of the working portion 5 during the first action described in the first embodiment will be referred to as F3, and a threshold level for force applied to the arm holder 51 of the working portion 5 in order to determine whether the doctor is mounting the right arm A on the arm holder 51 will be referred to as F2A. In addition, a threshold level for force applied to the arm holder 51 of the working portion 5 during the second action will be referred to as F1.

For example, in the fifth embodiment, the relationship between the threshold levels F1, F2A, and F3 preferably meets the following equation:

$$TW \geq F1 > F3 > F2A$$

For example, the threshold level F1 is set to 1.5 kgf (14.7 N), the threshold level F2A is set to 0.5 kgf (4.9 N), and the threshold level F3 is set to 1.0 kgf (9.8 N).

Referring to FIG. 12, the operations in steps S1 to S5 are performed in this order in the same manner as the first embodiment.

However, after the operation mode of the body support apparatus is set to the free mode (see step S3), when it is determined that the movement speed of the working portion 5 has been greater than the preset threshold level V for 100 ms (NO in step S4), the CPU 71 determines whether the right arm A is mounted on the arm holder 51 of the working portion 5 in the following operation in step S27.

Specifically, in step S27, the CPU 71 determines, based on the measured force data and torque data sent from the force sensor 45, whether:

force applied to the arm holder 51 of the working portion 5, i.e. the working end 51GE of the second guide part 51G2, has been equal to or smaller than the second threshold level F2A of 0.5 kgf (4.9 N) for 50 ms; or torque applied to the arm holder 51 has been equal to or smaller than third threshold level Tr3 equal to 1.5 kg·cm (14.7 N·cm) corresponding to the second threshold level F2A for 50 ms.

Note that the condition whether force applied to the arm holder 51 of the working portion 5, i.e. the working end 51GE of the second guide part 51G2, has been equal to or smaller than the second threshold level F2A for 50 ms will be referred to as a fifth condition. Similarly, the condition whether torque applied to the arm holder 51 has been equal to or smaller than the third threshold level Tr3 equal to 1.5 kg·cm (14.7 N·cm) for 50 ms will be referred to as a sixth condition.

Upon determination that neither the fifth condition nor the sixth condition is satisfied (NO in step S27), the CPU 71 repeats the determination in step S4, thus maintaining the operation mode of the body support apparatus in the free mode.

Specifically, during the free mode, the CPU 71 determines whether the movement speed of the working portion 5 has not been equal to or lower than the preset threshold level V for 100 ms (see step S4), and determines whether at least one of the fifth condition and the sixth condition is satisfied until the movement speed of the working portion 5 has been equal to or greater than the preset threshold level V for 100 ms (see step S27).

Upon determination that the fifth condition or sixth condition is met until the movement speed of the working portion 5 has been equal to or lower than the preset threshold level V for 100 ms (see YES in step S27), the CPU 71 performs the operation in step S1, thus setting the operation mode of the body support apparatus to the wait mode.

Otherwise, upon determination that the movement speed of the working portion 5 has been equal to or lower than the preset threshold level V for 100 ms (YES in step S4), the CPU 71 carries out the operation in step S5, thus setting the operation mode of the body support apparatus to the lock mode (see step S5).

Following the operation in step S5, in step S26, the CPU 71 determines, based on the measured force data and torque data sent from the force sensor 45, whether:

force applied to the arm holder 51 of the working portion 5, i.e. the working end 51GE of the second guide part 51G2, has been equal to or smaller than the third threshold level F3 of 1.0 kgf (9.8 N) for 200 ms; or:

torque applied to the arm holder 51 has been equal to or smaller than the second threshold level Tr2 equal to 5 kg·cm (49 N·cm) for 200 ms; the second threshold level Tr2 corresponds to the third threshold level F3.

Note that, as described above, the condition whether force applied to the arm holder 51 of the working portion 5, i.e. the working end 51GE of the second guide part 51G2, has been equal to or smaller than the third threshold level F3 of 1.0 kgf (9.8 N) for 200 ms is referred to as the third condition. Similarly, the condition whether torque applied to the arm holder 51 has been equal to or smaller than the second threshold level Tr2 equal to 49 N·cm for 200 ms is referred to as the fourth condition.

Upon determination that at least one of the third condition and the fourth condition is satisfied, the CPU 71 determines that the doctor tries to shift the operation mode of the body support apparatus from the lock mode to the free mode (YES in step S26). Then, the CPU 71 carries out the operation in step S3, thus shifting the operation mode of the body support apparatus from the lock mode to the free mode (see step S3).

That is, like the fourth embodiment, the determination that force applied to the working portion 5 is equal to or smaller than the third threshold level F3 of 1.0 kgf (9.8 N) shows a state in which the doctor performs the first action to support the right arm A with the muscle of the right arm A. In the fifth embodiment, when it is determined that this state has been continued for 200 ins (YES in step S26), the operation mode of the body support apparatus is set to the free mode (see step 63).

Otherwise, neither the third condition nor the fourth condition is satisfied (NO in step S26), the CPU 71 repeats the determination in step S26, thus maintaining the operation mode of the body support apparatus in the lock mode.

Next, how the operation mode of the body support apparatus is shifted based on execution of the mode determination task will be described hereinafter with reference to FIG. 13.

While the operation mode of the body support apparatus is set to the wait mode (see step S1), when force applied to the arm holder 51 of the working portion 5 has been equal to or greater than the first threshold level F1 for 100 ms or torque applied to the arm holder 51 has been equal to or greater than the first threshold level Tr1 (YES in step S2), the operation mode of the body support apparatus 1 is shifted from the wait mode to the free mode (see step S3 in FIG. 12 and T21 in FIG. 13). While the operation mode of the body support apparatus is set to the free mode, flickered orange light is output from each of the first and second light sources 58 and 59 (see step S3).

During the free mode of the body support apparatus, when the movement speed of the working portion 5 has been equal to or lower than the preset threshold level V for 100 ms (YES in step S4), the operation mode of the body support apparatus is shifted from the free mode to the lock mode (see step S5 in FIG. 12 and T22 in FIG. 13). While the operation mode of the body support apparatus is set to the lock mode, continuous blue light is output from each of the first and second light sources 58 and 59 (see step S5).

During the lock mode of the body support apparatus, when force applied to the ant holder 51 of the working portion 5 has been equal to or greater than the third threshold level F3 for 200 ms or torque applied to the arm holder 51 has been equal to or greater than the second threshold level Tr2 for 200 ms (YES in step S26), the operation mode of the body support apparatus is shifted from the lock mode to the free mode (see steps S26 and S3 in FIG. 12 and T23 in FIG. 13).

During the free mode of the body support apparatus, when force applied to the arm holder 51 of the working portion 5 has been equal to or greater than the second threshold level F2A for 50 ms or torque applied to the arm holder 51 has been equal to or greater than the third threshold level Tr3 for 50 ms (YES in step S27), the operation mode of the body support apparatus 1 is shifted from the free mode to the wait mode (see steps S27 and S1 in FIG. 12 and T24 in FIG. 13). During the wait mode, continuous orange light is irradiated from each of the first and second light sources 58 and 59 (see step S1 in FIG. 12).

As described above, the body support apparatus according to the fifth embodiment makes it possible to automatically shift the operation mode thereof among the wait mode, the free mode, and the lock mode in this order according to how the doctor applies force to the right arm A and how long the doctor is applying force to the right arm A. This permits the doctor to smoothly perform surgical operations on the affected site.

In addition, the body support apparatus according to the fifth embodiment makes it possible to shift the operation mode from the lock mode to the free mode according to how the doctor applies force to the right arm A and how long the doctor is applying force to the right arm A. This configuration permits the doctor to further intuitively or subconsciously move the working portion 5. Moreover, the body support apparatus according to the fifth embodiment makes it possible to shift the operation mode from the free mode to the free mode according to how the doctor applies force to the right arm A and how long the doctor is applying force to the right arm A. This configuration permits the doctor to immediately replace a current surgical operation tool held by the right hand with another surgical operation tool.

In each of the first to fifth embodiments, the first light source 58, 84, and 85, the second light source 59, 38, or 39, the power supply source 78, the drivers 79, and the controller 7 serve as, for example, an operation-mode indicating system. In each of the first to fifth embodiments, the doctor serves as, for example, an operator, the affected site, i.e. the surgical operation region, of the patient serves as, for example, a predetermined site of an object, and an arm A serves as, for example, a part of a body of an operator. In each of the first to fifth embodiments, the working portion 5 serves as, for example, a mount portion on which a part of a body of an operator is mountable, and the multijoint arm 3 serves as, for example, a support member. The electromagnets 52 and the hold member 55 serve as, for example, a fixing member, and the brakes 31A, 32A, and 33A serve as, for example, a limiting member. In each of the first to fifth embodiments, the first light source 58, 84, or 85 serves as, for example, a first light emitting device, and the second light sources 59, 38, or 39 serves as, for example, a second light emitting device. In each of the first to fifth embodiments, the free mode serves as, for example, a first operation mode of the body support apparatus, and each of the wait mode and the lock mode serves as, for example, a second operation mode of the body support apparatus.

In each of the first to fifth embodiments, the encoders 31B, 32B, and 33B, and the force sensor 45 serve as, for example, a detector. In the third embodiment, the binocular surgical microscope 80 serves as, for example, an optical system, the left and right eyepieces 81 and 82 correspond to, for example, binocular eyepieces. In each of the first to fifth embodiments, the operations of the controller in steps S2, S4, and S6 serve as, for example, a determiner.

The present disclosure is not limited to the aforementioned embodiments, and various modifications of each embodiment can be performed within the scope of the present disclosure. For example, in the third embodiment, in place of the binocular surgical microscope 80, a binocular endoscope or stereoscopic glasses can be used.

The support member can be configured to support the mount portion to be movable by bend of at least one joint in only a predetermined direction.

In the fourth embodiment, the controller can be configured to shift the operation mode of the body support apparatus in a predetermined order according to operation of the foot switch 90. This permits the doctor to intentionally shift the operation mode of the body support apparatus to a desired one of the wait, free, and lock modes.

In each of the first to fifth embodiments, as a fixing member, the electromagnets 52 and the hold member 55 are used, but the present disclosure is not limited thereto. Specifically, one of various types of fixing members, such as an automatically and mechanically fixing member, can be used as a fixing member of the present disclosure. The first light emitting device and the second light emitting device can be integrated with each other. For example, the arm holder 51 can serve as a light emitting device of the present disclosure. In each of the first to fifth embodiments, the force sensor 45 is used to detect.

In each of the first to fifth embodiments, the force sensor 45 is configured to detect force applied to the arm holder 51 of the working portion 5, and torque applied to the arm holder 51; these detected force and torque are used for the controller 7 to determine whether to set the operation mode of the body support apparatus to one of the free mode, the wait mode, and the lock mode, in other words, to shift the operation mode from a current operation mode to another operation mode. However, in the present disclosure, the force sensor 45 can be configured to detect force applied to the electromagnets 52a and 52b, and torque applied to the electromagnets 52a and 52b.

Specifically, in each of the first to fifth embodiment, at least one detector of the present disclosure is configured to detect, as at least one parameter required for determining whether to set the operation mode of the body support apparatus to one of the free mode, the wait mode, and the lock mode, at least one of:

force applied from the arm A to at least one of the working portion 5 and the electromagnets 52;

torque applied from the arm A to at least one of the working portion 5 and the electromagnets 52;

a movement speed of at least one of the working portion 5 and the electromagnets 52;

an acceleration, i.e. the rate of change of the movement speed, of at least one of the working portion 5 and the electromagnets 52;

a position of at least one of the working portion 5 and the electromagnets 52; and a parameter indicative of whether and how the arm A is in contact with at least one of the working portion 5 and the electromagnets 52.

As at least one detector for detecting the parameter indicative of whether and how the arm A is in contact with at least one of the working portion 5 and the electromagnets 52, a contact pressure sensor can be used.

While illustrative embodiments of the present disclosure have been described herein, the present disclosure is not limited to the embodiments described herein, but includes any and all embodiments having modifications, omissions, combinations (e.g., of aspects across various embodiments), adaptations and/or alternations as would be appreciated by those in the art based on the present disclosure. The limitations in the claims are to be interpreted broadly based on the language employed in the claims and not limited to examples described in the present specification or during the prosecution of the application, which examples are to be construed as non-exclusive.

What is claimed is:

1. An operation-mode indicating system for a body support apparatus for performing an operation to a predetermined site of an object, in which the body support apparatus comprises:

a mount portion on which a part of a body of an operator is mountable;

a support member that has at least one joint and supports the mount portion to be movable by bending of the at least one joint;

a fixing member controllable to, when the part of the body is mounted on the mount portion, fix the mount portion to the part of the body to thereby cause the mount portion to follow movement of the part of the body; and a limiting member controllable to limit bending of the at least one joint to limit movement of the mount portion, the operation-mode indicating system comprising:

a controller controllably connected to the fixing member and the limiting member and switchably setting an operation mode of the body support apparatus in one of a first operation mode and a second operation mode, the controller, in the first operation mode, controlling the fixing member to fix the mount portion to the part of the body, and controlling the limiting member not to limit bending of the at least one joint to thereby cause the mount portion to be freely movable, the controller, in the second operation mode, controlling the fixing member to release a fixture of the mount portion to the part of the body, and controlling the limiting member to limit bending of the at least one joint to thereby limit movement of the mount portion; and a first light emitting device located within a peripheral visual field of the operator and controllably connected to the controller, the peripheral visual field being defined around a center visual field of the operator while the operator is looking at the predetermined site, the controller controlling the first light emitting device to emit first light in the first operation mode and second light in the second operation mode, the second light being visually distinguishable from the first light.

2. The operation-mode indicating system according to claim 1, further comprising:
a second light emitting device located out of the peripheral visual field of the operator and controllably connected to the controller,
the controller controlling the second light emitting device to emit the first light in the first operation mode and the second light in the second operation mode, the second light being visually distinguishable from the first light.

3. The operation-mode indicating system according to claim 1, further comprising:
a detector that detects at least one of force applied from the part of the body to at least one of the mount portion and the fixing member; torque applied from the part of the body to at least one of the mount portion and the fixing member; a movement speed of at least one of the mount portion and the fixing member; an acceleration of at least one of the mount portion and the fixing member; a position of at least one of the mount portion and the fixing member; and a parameter indicative of whether and how the part of the body is in contact with at least one of the mount portion and the fixing member,
wherein the controller:
further comprises a determiner that determines, based on a detected result of the detector, whether the operator tries to cause the mount portion to follow movement of the part of the body;
sets the operation mode of the body support apparatus to the first operation mode when it is determined that the operator tries to cause the mount portion to follow movement of the part of the body; and
sets the operation mode of the body support apparatus to the second operation mode when it is determined that the operator does not try to cause the mount portion to follow movement of the part of the body.

4. The operation-mode indicating system according to claim 1, wherein the peripheral visual field is defined around the center visual field of at least one eye of the operator that is binocularly looking at the predetermined site via an optical system.

5. The operation-mode indicating system according to claim 4, wherein the optical system has binocular eyepieces through which the operator is binocularly looking at the predetermined site, and the first light emitting device is removably attached to at least one of the eyepieces of the optical system.

6. The operation-mode indicating system according to claim 2, wherein:
the body support apparatus is composed of a first body support apparatus and a second body support apparatus;
each of the first body support apparatus and the second body support apparatus comprises the mount portion, the support member, the fixing member, and the limiting member;
the part of the body of the operator mountable on the mount portion of the first body support apparatus is a left hand of the operator;
the part of the body of the operator mountable on the mount portion of the second body support apparatus is a right hand of the operator;
the first light emitting device is composed of first light emitting devices, the first light emitting devices being provided for the respective first and second body support apparatuses;
the second light emitting device is composed of second light emitting devices, the second light emitting devices being provided for the respective first and second body support apparatuses; and
the controller controls the first light emitting module and the second light emitting module of each of the first and second body support apparatuses.

7. The operation-mode indicating system according to claim 3, wherein:
the detector detects the force applied from the part of the body to at least one of the mount portion and the fixing member, the torque applied from the part of the body to at least one of the mount portion and the fixing member, and the movement speed of at least one of the mount portion and the fixing member;
the determiner performs a determination that determines, based on the detected result of the detector, whether at least one of the force applied from the part of the body to at least one of the mount portion and the fixing member and the torque applied from the part of the body to at least one of the mount portion and the fixing member has been equal to or greater than a corresponding preset threshold for a preset time, thus determining whether the operator tries to cause the mount portion to follow movement of the part of the body according to a result of the performed determination; and
the controller:
sets the operation mode of the body support apparatus to the first operation mode when it is determined that at least one of the force applied from the part of the body to at least one of the mount portion and the fixing member and the torque applied from the part of the body to at least one of the mount portion and the fixing member has been equal to or greater than the corresponding preset threshold for the preset time; and
sets the operation mode of the body support apparatus to the second operation mode when it is determined that at least one of the force applied from the part of the body to at least one of the mount portion and the fixing member and the torque applied from the part of the body to at least one of the mount portion and the fixing member has not been equal to or greater than the corresponding preset threshold for the preset time.

8. A body support apparatus for performing an operation to a predetermined site of an object, the body support apparatus comprising:
a mount portion on which a part of a body of an operator is mountable;
a support member that has at least one joint and supports the mount portion to be movable by bending of the at least one joint;
a fixing member controllable to, when the part of the body is mounted on the mount portion, fix the mount portion to the part of the body to thereby cause the mount portion to follow movement of the part of the body;
a limiting member controllable to limit bending of the at least one joint to limit movement of the mount portion;
a controller controllably connected to the fixing member and the limiting member and switchably setting an operation mode of the body support apparatus in one of a first operation mode and a second operation mode,
the controller, in the first operation mode, controlling the fixing member to fix the mount portion to the part of the body, and controlling the limiting member not to limit bending of the at least one joint to thereby cause the mount portion to be freely movable, the controller, in the second operation mode, controlling the fixing member to release a fixture of the mount portion to the part of the body, and controlling the limiting member to limit bending of the at least one joint to thereby limit movement of the mount portion; and a first light emitting device located within a peripheral visual field of the operator and controllably connected to the controller, the peripheral visual field being defined around a center visual field of the operator while the operator is looking at the predetermined site, the controller controlling the first light emitting device to emit first light in the first operation mode and second light in the second operation mode, the second light being visually distinguishable from the first light.

9. The body support apparatus according to claim 8, further comprising:

a second light emitting device located out of the peripheral visual field of the operator and controllably connected to the controller, the controller controlling the second light emitting device to emit the first light in the first operation mode and the second light in the second operation mode, the second light being visually distinguishable from the first light.

10. The body support apparatus according to claim 8, further comprising:

a detector that detects at least one of: force applied from the part of the body to at least one of the mount portion and the fixing member; torque applied from the part of the body to at least one of the mount portion and the fixing member; a movement speed of at least one of the mount portion and the fixing member; an acceleration of at least one of the mount portion and the fixing member; a position of at least one of the mount portion and the fixing member; and a parameter indicative of whether and how the part of the body is in contact with at least one of the mount portion and the fixing member, wherein the controller:

further comprises a determiner that determines, based on a detected result of the detector, whether the operator tries to cause the mount portion to follow movement of the part of the body;

sets the operation mode of the body support apparatus to the first operation mode when it is determined that the operator tries to cause the mount portion to follow movement of the part of the body; and sets the operation mode of the body support apparatus to the second operation mode when it is determined that the operator does not try to cause the mount portion to follow movement of the part of the body.

11. The body support apparatus according to claim 8, wherein the peripheral visual field is defined around the center visual field of at least one eye of the operator that is binocularly looking at the predetermined site via an optical system.

12. The body support apparatus according to claim 11, wherein the optical system has binocular eyepieces through which the operator is binocularly looking at the predetermined site, and the first light emitting device is removably attached to at least one of the eyepieces of the optical system.

13. The body support apparatus according to claim 9, wherein:

the body support apparatus is composed of a first body support apparatus and a second body support apparatus;

each of the first body support apparatus and the second body support apparatus comprises the mount portion, the support member, the fixing member, the limiting member, the first light emitting device, and the second light emitting device;

the part of the body of the operator mountable on the mount portion of the first body support apparatus is a left hand of the operator; and the controller is shared by the first and second body support apparatuses, and configured to control the first light emitting module and the second light emitting module of each of the first and second body support apparatuses.

14. The body support apparatus according to claim 10, wherein:

the detector detects the force applied from the part of the body to at least one of the mount portion and the fixing member, the torque applied from the part of the body to at least one of the mount portion and the fixing member, and the movement speed of at least one of the mount portion and the fixing member;

the determiner performs a determination that determines, based on the detected result of the detector, whether at least one of the force applied from the part of the body to at least one of the mount portion and the fixing member and the torque applied from the part of the body to at least one of the mount portion and the fixing member has been equal to or greater than a corresponding preset threshold for a preset time thus determining whether the operator tries to cause the mount portion to follow movement of the part of the body according to a result of the performed determination; and the controller:

sets the operation mode of the body support apparatus to the first operation mode when it is determined that at least one of the force applied from the part of the body to at least one of the mount portion and the fixing member and the torque applied from the part of the body to at least one of the mount portion and the fixing member has been equal to or greater than the corresponding preset threshold for the preset time; and sets the operation mode of the body support apparatus to the second operation mode when it is determined that at least one of the force applied from the part of the body to at least one of the mount portion and the fixing member and the torque applied from the part of the body to at least one of the mount portion and the fixing member has not been equal to or greater than the corresponding preset threshold for the preset time.

* * * * *